United States Patent
Kriesel et al.

(10) Patent No.: US 12,286,805 B1
(45) Date of Patent: Apr. 29, 2025

(54) ARTICULATING MEDICAL STAND

(71) Applicant: Universal Tech Corporation, Ettrick, WI (US)

(72) Inventors: Matthew Wayne Kriesel, Melrose, WI (US); Troy Bradley Goodenough, Mindoro, WI (US)

(73) Assignee: Universal Tech Corporation, Ettrick, WI (US)

( * ) Notice: Subject to any disclaimer, the term of this patent is extended or adjusted under 35 U.S.C. 154(b) by 0 days.

(21) Appl. No.: 17/991,841

(22) Filed: Nov. 21, 2022

Related U.S. Application Data

(63) Continuation of application No. 15/932,829, filed on May 3, 2018, now Pat. No. 11,505,956, which is a
(Continued)

(51) Int. Cl.
*E04G 23/02* (2006.01)
*A61B 50/33* (2016.01)
(Continued)

(52) U.S. Cl.
CPC .......... *E04G 23/0214* (2013.01); *A61B 50/33* (2016.02); *B32B 7/12* (2013.01);
(Continued)

(58) Field of Classification Search
None
See application file for complete search history.

(56) References Cited

U.S. PATENT DOCUMENTS

| | | | |
|---|---|---|---|
| 3,507,071 | A | 4/1970 | Bryson |
| 5,677,413 | A | 10/1997 | Barksby et al. |

(Continued)

FOREIGN PATENT DOCUMENTS

| | | | | | |
|---|---|---|---|---|---|
| CA | 3025590 A1 | * | 1/2018 | ............. | A61B 50/30 |
| CA | 3038004 A1 | * | 4/2018 | ............. | A61B 50/10 |

*Primary Examiner* — Jeffrey D Washville
(74) *Attorney, Agent, or Firm* — BRRLaw LLC; Bryan R. Rosiejka

(57) ABSTRACT

An inventive articulating medical stand comprises a lower horizontal support member, a vertical support member, an upper horizontal support member, a tray mounting member and an adhesive medical tray member. The vertical support member is connected to the lower horizontal support member and is capable of vertical height adjustment, and optionally axial rotational adjustment. One end of the upper horizontal support member is connected to the vertical support member and is capable of axial rotational adjustment. The tray mounting member is slideably connected to the upper horizontal support member and is capable of linear adjustment along the longitudinal length of the upper horizontal support member. The tray mounting member is also capable of angular rotational adjustment with respect to the longitudinal axis of the upper horizontal support member. The adhesive medical tray member is removably connected to the tray mounting member and comprises a releasably adhesive component for attachment of medical items. Accordingly, the articulating medical stand is configured such that the adhesive medical tray member can be adjusted through all axes of dimension.

33 Claims, 9 Drawing Sheets

Related U.S. Application Data continuation-in-part of application No. 15/731,815, filed on Aug. 7, 2017, now Pat. No. 11,124,596, which is a continuation-in-part of application No. 14/999,722, filed on Jun. 20, 2016, now Pat. No. 10,807,767.

(60) Provisional application No. 62/231,004, filed on Jun. 22, 2015.

(51) Int. Cl.
*B32B 7/12* (2006.01)
*B41J 2/01* (2006.01)
*B65D 1/34* (2006.01)
*C08G 18/10* (2006.01)
*C08G 18/36* (2006.01)
*C08G 18/48* (2006.01)
*G06K 15/02* (2006.01)

(52) U.S. Cl.
CPC ............ *B65D 1/34* (2013.01); *E04G 23/0285* (2013.01); *G06K 15/02* (2013.01); *B41J 2/01* (2013.01); *C08G 18/10* (2013.01); *C08G 18/36* (2013.01); *C08G 18/4825* (2013.01); *C08G 18/4829* (2013.01)

(56) References Cited

U.S. PATENT DOCUMENTS

| | | |
|---|---|---|
| 5,864,001 A | 1/1999 | Masse et al. |
| 6,673,409 B1 | 1/2004 | Wheatley |
| 7,041,719 B2 | 10/2006 | Wheatley |
| 7,125,602 B2 | 10/2006 | Wheatley |
| 7,252,867 B2 | 8/2007 | Wheatley |
| 7,910,188 B2 | 3/2011 | Wheatley |
| 7,923,088 B2 | 4/2011 | Wheatley |
| 8,110,269 B2 | 2/2012 | Wheatley |
| 8,110,270 B2 | 2/2012 | Wheatley |
| 2008/0005929 A1 | 1/2008 | Hardy et al. |
| 2010/0170139 A1 | 7/2010 | Zhou |
| 2013/0288060 A1 | 10/2013 | Pind et al. |
| 2013/0296449 A1 | 11/2013 | Peterson et al. |
| 2015/0053583 A1 | 2/2015 | McCormick et al. |

\* cited by examiner

ARTICULATING MEDICAL STAND

CROSS-REFERENCE TO RELATED APPLICATION

This application is a Continuation-In-Part of, and claims priority to, U.S. Nonprovisional application Ser. No. 15/932,829 filed May 3, 2018, which is a Continuation-In-Part of U.S. Nonprovisional application Ser. No. 15/731,815 filed Aug. 7, 2017, which is a Continuation-In-Part of U.S. Nonprovisional application Ser. No. 14/999,722 filed Jun. 20, 2016, which is a Nonprovisional application of U.S. Provisional Application No. 62/231,004 filed Jun. 22, 2015, all of which applications are incorporated herein by reference in their entirety.

TECHNICAL FIELD

The present disclosure relates to portable medical stands for medical instruments, such as Mayo stands, for example. In some more particular embodiments, the present invention relates to medical stands having one or more articulating components for presenting such medical instruments via a releasably adhesive medical tray member. In some preferred embodiments, the adhesive medical tray member comprises a releasably adhesive and cohesive viscoelastomeric thermoset polymer component disposed thereon.

BACKGROUND

During medical procedures, such as surgery for example, medical professionals (e.g., surgeons) typically desire having their medical instruments and supplies located at or near the location of a particular medical procedure. To achieve this, such medical professionals often utilize a medical stand, and most typically a Mayo stand. Conventional Mayo stands typically include a removable medical tray which is set on a movable stand that is positioned over or adjacent to a surgical site. Such Mayo stands also provide a place for setting sterile instruments and supplies used during surgery. Conventional Mayo stands typically have a general "C-shape", which includes a vertical portion having a top end and a bottom end, a first horizontal portion attached to or integral with the bottom end of the vertical portion, and a second horizontal portion attached to or integral with the top end of the vertical portion. Typically, the first (lower) horizontal portion will include at least two casters which allow the stand to be moveable, and may optionally also include one or more legs which can help maintain the stand in a resting position during use. Typically, the second (upper) horizontal portion will be configured to accept a medical tray upon which medical instruments and supplies can be loosely placed. Such a medical tray typically has a flat planar surface and often includes minimal side edges to help prevent medical instruments and supplies from readily rolling off the tray. Typically, conventional Mayo stands do not allow for any adjustment to the dimensions thereof, although some conventional Mayo stands may allow for a height adjustment via the vertical portion.

The general C-shape of conventional Mayo stands optionally allows the stand to be positioned integral with a surgical bed, such that the first (lower) horizontal portion is located beneath the bed, and the second (upper) horizontal portion is located above a patient lying in the bed. However, such conventional Mayo stands are more typically placed at a location proximate to the bed. During use (such as during a surgical procedure), a scrub nurse typically is required to "hand-off" particular medical instruments and supplies to the surgeon as they are needed, and then further replaces such items back onto the Mayo stand when the use is completed.

Unfortunately, conventional medical stands have several deficiencies. For example, one such deficiency is that the medical tray portion of conventional medical stands allows for movement of the medical instruments and supplies disposed thereon. This can lead to such items undesirably repositioning out of order, cross-contamination of such items, and items falling off the tray, all of which require extra time and potentially the replacement of such items with new items. Thus, there is a need for a medical stand that prevents the movement of medical instruments and supplies disposed thereon.

Another deficiency of conventional medical stands is that the tray portion (i.e., the second (upper) horizontal portion) of conventional medical stands cannot be conveniently or ergonomically angled. Rather, conventional medical stands (e.g., Mayo stands) remain horizontal, including those stands that allow for a height adjustment. Such horizontal orientation is less than ideal for a user, including convenience, comfort and ergonomics, but is a necessity since any attempt to position conventional medical stands at an angle would result in the medical instruments and supplies moving and conglomerating at the bottom of an angled medical tray member. Thus, there is a need for a medical stand wherein the medical tray member can be angled during use substantially without movement or repositioning of the medical instruments and supplies disposed thereon.

Yet another deficiency of conventional medical stands is that during medical procedures (e.g., surgical procedures), conventional medical stands often get bumped or jarred due to activity by the people involved with the medical procedure or by the movement of other equipment. This often results in one or more medical instruments or supplies falling off the conventional medical stand, thus becoming contaminated. Such fallen items must then be replaced, which is both costly and time consuming. Thus, there is a need for a medical stand that can maintain the medical instruments and supplies placed thereon in a securely attached position upon the medical stand until such item is required for use.

Still another deficiency of conventional medical stands is that, in most instances, at least two people are required when utilizing a conventional medical stand during a medical procedure (e.g., surgery). This typically includes a primary medical professional (e.g., surgeon) who calls for and utilizes an item stored upon the medical stand during a procedure, and an additional medical professional (e.g., a scrub nurse) who then picks-up the requested item from the conventional medical stand and hands the item to the surgeon, and then subsequently retrieves the item from the surgeon after use and replaces the item onto the medical stand. Not only is this process inefficient, but it also often results in the dropping (and thus the contamination) of a medical instrument or supply, which must then be replaced or re-sterilized (which is both costly and time consuming). Thus, there is a need for a medical stand that can be conveniently positioned for the primary medical professional (e.g., surgeon) such that an additional medical professional is not required and/or which reduces or eliminates incidents of dropping medical instruments and supplies.

SUMMARY

The invention of the present disclosure solves one or more of the problems enumerated above.

In some preferred embodiments, an articulating medical stand comprises a lower horizontal support member, a vertical support member and an upper horizontal support member. The lower horizontal support member comprises a top side and an opposing bottom side distal to the top side. The vertical support member comprises an upper end, an opposing lower end distal to the upper end, a longitudinal length and a longitudinal axis. The upper horizontal support member comprises a first end, an opposing second end distal to the first end, a longitudinal length and a longitudinal axis. In addition, the lower end of the vertical support member is attached to the top side of the lower horizontal support member. Also, the first end of the upper horizontal support member is attached proximate to the upper end of the vertical support member. Furthermore, the vertical support member is vertically adjustable along its longitudinal length. In addition, the upper horizontal support member is axially rotatable about its longitudinal axis.

In some aspects of this embodiment, the vertical support member is axially rotatable about its longitudinal axis. In other aspects, the articulating medical stand further comprises a tray mounting member. In further aspects, the tray mounting member comprises a housing support element, an adjustable connector element, and a tray receiving element, where the housing support element is slideably connected to the upper horizontal support member such that the tray mounting member can be repositioned along the longitudinal length of the upper horizontal support member and the tray mounting member can further rotate with the upper horizontal support member. In addition, the adjustable connector element is attached to the housing support element, and the tray receiving element is attached to the adjustable connector element. Furthermore, the adjustable connector element is capable of providing angular adjustment of the tray receiving element. In addition, the tray receiving element is adapted to receive a medical tray member. In some additional aspects, the tray receiving element further comprises a crossbeam support component. In further aspects, the tray receiving element is attached to the adjustable connector element via the crossbeam support component.

In some aspects of this embodiment, the articulating medical stand is in the form of an articulating Mayo stand.

In some aspects of this embodiment, the articulating medical stand further comprises a medical tray member, where the medical tray member is removably attached to the tray mounting member. In some further aspects, the medical tray member is in the form of an adhesive medical tray member. In still further aspects, the adhesive medical tray member comprises a top side and a bottom side, and an adhesive component is disposed upon at least a portion of the top side of the adhesive medical tray member. In some additional aspects, the adhesive medical tray member further comprises a side element disposed upon at least a portion of a perimeter of the top side of the adhesive medical tray member. In further aspects, the adhesive medical tray member further comprises a lip element disposed upon an upper edge portion of the side element.

In some aspects of this embodiment, the adhesive medical tray comprises an adhesiveness of about 25 $g_f/cm^2$ to about 150 $g_f/cm^2$ as measured by the Adhesiveness & Cohesiveness Test.

In some aspects of this embodiment, the adhesive medical tray member comprises an adhesive component thickness of about 0.5 mm to about 13 mm.

In some aspects of this embodiment, the adhesive component comprises a releasably adhesive and cohesive viscoelastomeric thermoset polymer component. In some further aspects, the releasably adhesive and cohesive viscoelastomeric thermoset polymer component is formed from a thermosetting reaction media comprising:
  A. about 2 wt % to about 10 wt % isocyanate prepolymer;
  B. about 35 wt % to about 75 wt % polyols; and
  C. about 10 wt % to about 60 wt % plasticizer;
where the polyols comprise about 1 wt % to about 65 wt % straight chain polyols based on the total reaction media weight and about 3 wt % to about 50 wt % crosslinking polyols based on the total reaction media weight, and where the plasticizer comprises about 10 wt % to less than about 45 wt % epoxidized triglyceride plasticizer based on the total reaction media weight and 0 wt % to about 40 wt % viscosity-reducing plasticizer based on the total reaction media weight. In some aspects, the isocyanate prepolymer comprises diisocyanate. In other aspects, the thermosetting reaction media further comprises a straight chain polyol to crosslinking polyol weight ratio of about 3:1 to about 1:3. In yet other aspects, the straight chain polyols comprise polyether diol and the crosslinking polyols comprise polyether triol. In still other aspects, the epoxidized triglyceride plasticizer comprises epoxidized vegetable oil plasticizer. In yet other aspects, the viscosity-reducing plasticizer comprises an ester plasticizer.

In some aspects of this embodiment, the releasably adhesive and cohesive viscoelastomeric thermoset polymer component is applied to the adhesive medical tray member in a prefabricated form. In other aspects, the thermosetting reaction media has been disposed upon the top side of the adhesive medical tray member while in liquid form, and then allowed to fully cure in situ to form the releasably adhesive and cohesive viscoelastomeric thermoset polymer component.

In some aspects of this embodiment, the adhesive medical tray member further comprises releasably adhesive and cohesive viscoelastomeric thermoset polymer component disposed upon the bottom side.

In some preferred embodiments, a method of making an articulated medical stand, comprises:
  A. providing a lower horizontal support member comprising a top side and a bottom side;
  B. providing a vertical support member comprising a lower end, an upper end, and a longitudinal axis, where the vertical support member is capable of vertical length adjustment along the longitudinal axis;
  C. providing an upper horizontal support member comprising a first end, a second end, a longitudinal axis and a longitudinal length, where the horizontal support member is capable of axial rotational adjustment about the longitudinal axis;
  D. providing a tray mounting member comprising a housing support element, an adjustable connector element, and a tray receiving element;
  E. providing an adhesive medical tray member comprising a top side and a bottom side, where the top side of the adhesive medical tray member comprises an adhesive component capable of releasably attaching medical items;
  F. attaching the lower end of the vertical support member to the top side of the lower horizontal support member;
  G. attaching the first end of the upper horizontal support member proximate to the upper end of the vertical support member;
  H. slideably attaching the housing support element of the tray mounting member to the upper horizontal support member; and I. removably attaching the adhesive medical tray member to the tray receiving element of the tray mounting member;

In this embodiment, the tray mounting member is capable of longitudinal adjustment along the longitudinal length of the upper horizontal support member. Also, the tray mounting member can rotate with the upper horizontal support member. In addition, the tray mounting member is capable of angular adjustment with respect to the upper horizontal support member.

In some aspects of this embodiment, the adhesive component comprises a releasably adhesive and cohesive viscoelastomeric thermoset polymer component. In some further aspects, the releasably adhesive and cohesive viscoelastomeric thermoset polymer component is formed from a thermosetting reaction media comprising:
  A. about 2 wt % to about 10 wt % isocyanate prepolymer;
  B. about 35 wt % to about 75 wt % polyols; and
  C. about 10 wt % to about 60 wt % plasticizer;
where the polyols comprise about 1 wt % to about 65 wt % straight chain polyols based on the total reaction media weight and about 3 wt % to about 50 wt % crosslinking polyols based on the total reaction media weight, and where the plasticizer comprises about 10 wt % to less than about 45 wt % epoxidized triglyceride plasticizer based on the total reaction media weight and 0 wt % to about 40 wt % viscosity-reducing plasticizer based on the total reaction media weight.

In some aspects of this embodiment, the adhesive medical tray comprises an adhesiveness of about 25 $g_f/cm^2$ to about 150 $g_f/cm^2$ as measured by the Adhesiveness & Cohesiveness Test.

In some preferred embodiments, a method for using an articulating medical stand comprises:
  A. Providing an articulating medical stand comprising a lower horizontal support member having a top side and a bottom side, a vertical support member comprising a lower end, an upper end and a longitudinal axis wherein the lower end is attached to the top side of the lower horizontal support member, an upper horizontal support member comprising a first end, a second end, a longitudinal axis and a longitudinal length wherein the first end is attached proximate to the upper end of the vertical support member, and a tray mounting member comprising a housing support element, an adjustable connector element, and a tray receiving element wherein the housing support element is slideably connected to the upper horizontal support member;
  B. providing an adhesive medical tray member comprising a tray component having a top side and a bottom side, and further comprising an adhesive component disposed upon the top side thereof;
  C. attaching the adhesive medical tray member to the tray receiving element of the tray mounting member to form the articulating medical stand;
  D. disposing medical items upon the top side of the adhesive medical tray member to form releasably attached medical items;
  E. multi-directionally adjusting the articulating medical stand such that the attached medical items are located at a desired location with respect to the user; and
  F. detaching a medical item from the adhesive medical tray member of the articulating medical stand for use;

In this embodiment, the vertical support member is capable of vertical adjustment along its longitudinal axis. Also, the upper horizontal support member is capable of axial rotational adjustment about its longitudinal axis. In addition, the tray mounting member is capable of linear adjustment along the longitudinal length of the upper horizontal support member. Furthermore, the tray mounting member is capable of rotational adjustment via the upper horizontal support member. In addition, the tray mounting member is capable of angular adjustment with respect to the upper horizontal support member.

In some aspects of this embodiment, the method further comprises re-attaching the medical item to the adhesive medical tray member of the articulating medical stand after use.

In some aspects of this embodiment, the vertical support member is further capable of axial rotational adjustment about its longitudinal axis.

In some aspects of this embodiment, the adhesive component comprises a releasably adhesive and cohesive viscoelastomeric thermoset polymer component. In some further aspects, the releasably adhesive and cohesive viscoelastomeric thermoset polymer component is formed from a thermosetting reaction media comprising:
  A. about 2 wt % to about 10 wt % isocyanate prepolymer;
  B. about 35 wt % to about 75 wt % polyols; and
  C. about 10 wt % to about 60 wt % plasticizer;
where the polyols comprise about 1 wt % to about 65 wt % straight chain polyols based on the total reaction media weight and about 3 wt % to about 50 wt % crosslinking polyols based on the total reaction media weight, and where the plasticizer comprises about 10 wt % to less than about 45 wt % epoxidized triglyceride plasticizer based on the total reaction media weight and 0 wt % to about 40 wt % viscosity-reducing plasticizer based on the total reaction media weight.

In some aspects of this embodiment, the adhesive medical tray of the articulating medical stand comprises an adhesiveness of about 25 $g_f/cm^2$ to about 150 $g_f/cm^2$ as measured by the Adhesiveness & Cohesiveness Test.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention.

In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

FIGURES

The foregoing and other features, aspects and advantages of the present invention will become better understood with regard to the following description, appended claims and accompanying drawings where:

Figure 1:
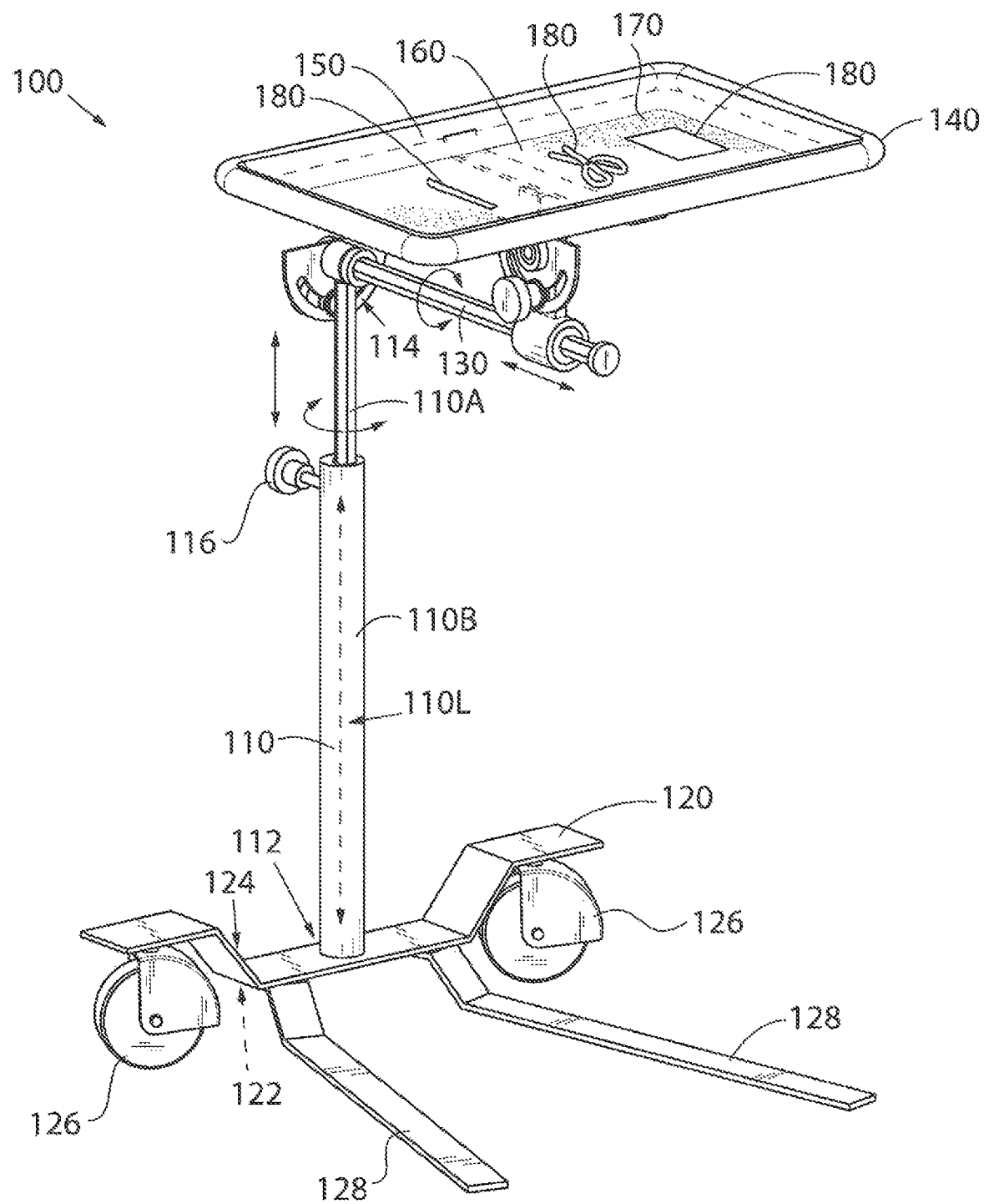
FIG. 1 is a perspective view showing a non-limiting exemplary embodiment of an inventive articulating medical stand of the present disclosure.

Repeated use of reference characters in the present specification and drawings is intended to represent the same or analogous features or elements of the present invention. It should be understood that the drawings herein are not intended to be drawn to scale, but rather are drawn to show particular elements of the invention.

TEST METHODS

Adhesiveness & Cohesiveness Test

Figure 8:
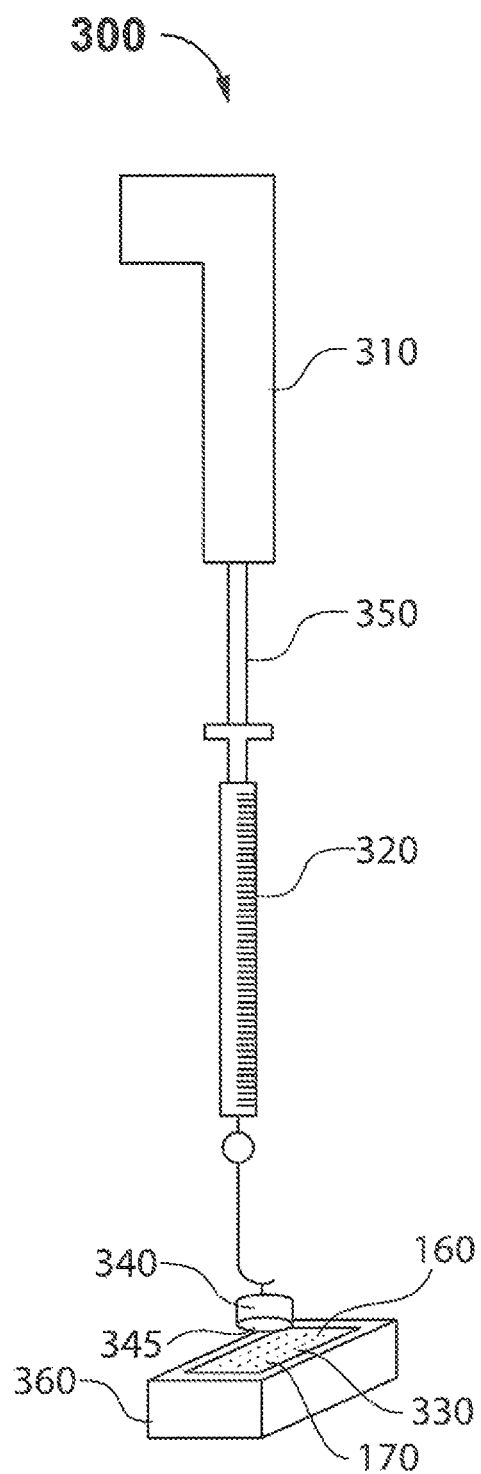
FIG. 8 is a front perspective view showing a testing apparatus for the Adhesiveness & Cohesiveness Test.

Referring to FIG. 8, the illustrated testing apparatus 300 can be utilized for testing the adhesiveness, cohesiveness and releasability properties of various adhesive components 160. The test apparatus 300 includes a motor driven actuator 310 (similar in concept to that of a standard remote controlled electric garage door opener, such as a Model 3265, available from The Chamberlain Group, Inc., having a place of business located in Elmhurst, Illinois 60126, U.S.A.) or equivalent. The actuator 310 includes a reversible constant speed motor (2.7 cm/sec which is occluded from view) serving to drive a remotely controlled reciprocating test probe 350 connected to a measuring scale 320 to measure adhesiveness, which is the amount of applied force (in grams-force) needed to separate each test sample 330 from a polished nickel cylinder 340 weighing 20.0 grams and having a contact surface area 345 of 1.76 cm², thus providing measurements in units of grams-force per square centimeter ($g_f/cm^2$). A testing platform 360 of a laterally movable form is utilized to provide a solid, flat and level surface which allows for repositioning of the test sample 330 to provide accurate repetitions of the test results for each tested sample. Such testing platform 360 should be compatible with the adhesion of the test sample 330 such that it can hold the test sample 330 thereto, and should be of a sufficient weight such that it does not lift from the surface during testing. The testing platform 360 may thus be repositioned to provide a repetition of an untested portion of the test sample 330 for further testing. Accordingly, adhesiveness is measured as the average of ten (10) repetitions upon untested portions of a single test sample 330.

The testing procedure is also useful for determining the cohesiveness of the test sample 330. This is accomplished by visually observing and noting the presence or absence of polymeric residue from test sample 330 upon the test cylinder surface 345 after separating the cylinder 340 from the test sample 330 via the test procedure. The cylinder surface 345 should be cleaned of any residue between each repetition, and the cohesiveness is measured as the average amount of residue over ten (10) repetitions upon untested portions of a single test sample 330.

In addition, additional testing can include the application of pressure to the cylinder 340 when in contact with a test sample 330. By measuring the adhesiveness and cohesiveness of each test sample 330 under differently applied sample application pressures, the adhesive and cohesive effects from applying such different pressures can likewise be determined.

Additionally, adhesiveness changes measured over timed sequence intervals can also be determined so as to provide adhesiveness data upon a test sample's 330 adhesiveness stability. The test procedure can also be utilized to provide adhesiveness data upon short interval adhesiveness increases following an initial adhesive attachment of the cylinder surface 345 to the test sample 330. Differences in adhesiveness between a pressure applied test probe and a non-pressure applied test probe over timed intervals can also be determined.

Continuing with FIG. 8, the following more detailed methodology can be utilized to test the adhesiveness and cohesiveness of various test samples 330:

1. Scope
   1.1. This method measures the level of tackiness (adhesiveness) exhibited by adhesive materials and the cohesiveness of such materials, optionally taking into account time dependent and/or pressure dependent adhesiveness properties.
   1.2. This test is designed for use with materials that exhibit adhesive properties, but may also be used with materials not explicitly classified as adhesives, including but not limited to materials having adhesive-like properties.
   1.3. Units—The tested values of adhesiveness are based upon grams-force per square centimeter ($g_f/cm^2$) of the force needed to separate the surface 345 of a polished nickel cylinder 340 having a contact surface area of 1.76 cm² from the test sample 330.

2. Terminology
   2.1. As used herein, the term "adhesive-like" refers to having a sticky quality akin to an adhesive, but which derives its sticky quality from a molecular structure that forms a molecular attraction (e.g., rather than adhesive or chemical bonded properties) which is releasable from adhered objects.
   2.2. As used herein, the term "tackiness" refers to the adhesiveness quality of feeling sticky to the touch.

2.3. As used herein, the term "time dependent adhesive" refers to a material in which adhesive strength changes according to duration of the contact time with a contacting surface.

2.4. As used herein, the term "pressure sensitive adhesives" refers to a material wherein additional external pressure is required to achieve a change in adhesiveness after initial contact.

3. Summary of Test Method Using the Testing Apparatus Depicted in FIG. 8

3.1. A test sample 330 the adhesive component 160 is placed upon the top side planar surface of the testing platform 360 and secured thereto.

3.2. The reciprocating testing probe 350 of the apparatus 300 is lowered to place the surface 345 of the cylinder 340 onto the test sample 330.

3.3. The surface 345 of the cylinder 340 of the apparatus 300 should remain in contact with the test sample 330 for a designated time period (typically 15 seconds).

3.4. The cylinder 340 of the apparatus 300 is then raised from the test sample 330 via the reciprocating test probe 350 at a constant speed of 2.7 cm/sec to measure the force in grams required to completely separate the cylinder surface 345 from the test sample 330, as indicated by the measuring scale 320.

3.5. The measured separating force (adhesiveness) is then calculated and recorded in units of $g_f/cm^2$. In addition, the contacting surface 345 of the cylinder 340 is visually inspected and the amount (e.g., the weight) of residue attached thereto (if any) is recorded to determine cohesiveness. (Note: the surface 345 should be cleaned if residue from the adhesive component 160 is present prior to further testing.)

3.6. Steps 3.1-3.5 are then repeated on untested portions of the test sample 330 so as to obtain a total of ten (10) tests per test sample 330, which are then averaged to yield a final result.

3.7. Optionally, steps 3.1-3.6 can then be repeated over designated contact time intervals so as to determine time dependent properties of a test sample 330.

3.8. Optionally, steps 3.1-3.6 can then be repeated over designated applied pressures so as to determine pressure dependent properties of a test sample 330.

4. Apparatus 4.1. The testing apparatus 300 is illustrated in FIG. 8. Equivalent materials and configurations to those stipulated may be utilized as long as they achieve comparable performance and meet the performance stipulations outlined in Section 4.2 below. Key elements of the apparatus include:

4.1.1. A reciprocating test probe 350, which is responsible for lowering and raising the cylinder 340 onto the material sample 330 at a constant speed of 2.7 cm/sec.

4.1.2. The scale 320, which measures the amount of force in grams required to separate the contact surface 345 of the cylinder 340 from the test sample 330.

4.1.3. The cylinder 340 which weighs 20.0 grams, and the contact surface 345 of the cylinder 340, which is the sole contacting surface with the test sample 330. The contact surface 345 of the cylinder 340 is a circular polished nickel surface having a total contact surface area of 1.76 cm².

4.1.4. The testing platform 360, which provides a solid, level surface for accurate test results and upon which the test sample 330 is secured for testing. This platform 360 is laterally movable so as to allow for repositioning of the test sample 330 for multiple testing.

4.2. Regardless of the specific components used:

4.2.1. The motor driven actuator 310 must actuate the reciprocating test probe 350 so as to raise and lower the cylinder 340 at a constant speed of 2.70 cm/second.

4.2.2. The accuracy of the Test, the testing apparatus 300 and scale 320 must measure force in grams with an accuracy resolution of five-percent (5%) or better.

4.2.3. Except for optional pressure applied tests, a constant pressure of 20.0 grams for the duration of the Test must be applied by the free-hanging, weighted cylinder 340.

4.3. The test procedure is conducted at ambient temperatures of 18° C. to 24° C. and most preferably at 21° C.

5. Calibration 5.1. Prior to first use and at subsequent reasonable testing intervals afterwards, the speed rate of the reciprocating test probe 350 is verified (and adjusted as needed) to ensure consistency within the standard outlined in Section 4.2.1.

5.2. Prior to first use, the accuracy of the scale 320 should be verified against a known weight and adjusted or zeroed accordingly.

6. Procedure 6.1. Assemble the testing apparatus 300.

6.2. Secure a test sample 330 of the adhesive component 160 upon the top side planar surface of the testing platform 360, ensuring that the platform 360 does not lift free during testing.

6.3. Lower the free hanging testing cylinder 340 onto the top side of the test sample 330, ensuring even contact between the contact surface 345 and the test sample 330, and ensuring the reciprocating test probe 350 and testing scale 350 are neither pulling nor applying pressure to the cylinder 340.

6.4. Allow the surface 345 of the cylinder 340 to remain in contact with the test sample 330 for 15 seconds or for the duration of another predetermined contact period.

6.5. Continue the test by raising the surface 345 of the cylinder 340 from the test sample 330 until the surface 345 has completely separated from the test sample 330.

6.6. Record the amount of gram-force as measured by the scale 350 required to completely separate the surface 345 of the cylinder 340 from the test sample 330.

6.7. Clean the surface 345 of the cylinder 340 after each iteration with a lint free cloth.

6.8. Reset the scale 350.

6.9. Reposition the testing platform 360 such that a fresh (untested) area of the test sample 330 is tested by the apparatus 300.

6.10. Repeat steps 6.2-6.9 to obtain a total of ten (10) measurements.

6.11. Optionally repeat steps 6.2-6.10 for each duration of testing to determine time dependent properties (e.g., at timed intervals 15 seconds, 30 seconds, 5 minutes, 10 minutes and 15 minutes).

6.12. Optionally repeat steps 6.2-6.10 for each duration of testing to determine pressure dependent properties (by applying incremental predetermined pressures to the cylinder 340).

7. Calculation and Interpretation of Results 7.1. Calculate the adhesiveness for each of the ten (10) test sample 330 measurements by dividing the force ($g_f$) required for the surface 345 of the cylinder 340 to completely detach from the test sample 330 by the contact surface area 345 of the cylinder 740 (1.76 cm²), and then calculate the average of the ten (10) adhesiveness measurements to establish a final adhesiveness value. The average tested value is given in the amount of grams-force per square centimeter ($g_f/cm^2$) representing the required force to completely separate the surface 345 of the cylinder 340 from the test sample 330, which serves as a measurement of adhesiveness.

7.2. Weigh the amount of adhesive component 160 residue observed on the surface 345 of the cylinder 340 for each of the ten (10) test repetitions, and then calculate the average of the ten (10) quantities to establish a final average residue weight. Divide the average residue weight by the area of the surface 345 of the cylinder 340 to obtain a cohesiveness value. A lower cohesiveness value is more desirable than a higher value (e.g., wherein a lower value indicates less residue transferred to the contacting surface 345 of the cylinder 340 (i.e., better cohesiveness) than a higher value).

7.3. Repeat steps 7.1 and 7.2 for all iterations tested.

Peel Test

In addition to the Adhesiveness & Cohesiveness Test described above, adhesiveness, cohesiveness and releasability properties can additionally be measured using standardized test methods known to persons having skill in the art, such as ASTM D1876 Peel Resistance of Adhesives (T-Peel Test), as well as other standardized Peel Tests, such as the ASTM 90-Degree Test and ASTM 180-Degree Test, which are used when a flexible material has been bonded to a rigid substrate such as plastic or metal, as well as equivalent tests thereof.

DEFINITIONS

It should be noted that, when employed in the present disclosure, the terms "a" and "an" are intended to mean "at least one" of any stated features, elements, integers, steps, components, or groups and are not intended to be limited to only one of such features, elements, integers, steps, components, or groups thereof, except where specifically stated as such. In addition, use of the phrase "at least one" is not intended to render other uses of the terms "a" or "an" to be limited to only one of a feature, element, integer, step, component, or group.

It should be noted that, when employed in the present disclosure, the terms "comprises," "comprising" and other derivatives from the root term "comprise" are intended to be open ended terms that specify the presence of any stated features, elements, integers, steps, components, or groups, and are not intended to preclude the presence or addition of one or more other features, elements, integers, steps, components, or groups thereof.

As used herein, the terms "adhesive" and "adhesiveness" refer to the bonding strength or adhesive release strength of the adhesive component of the present disclosure to an object. Adhesiveness can be measured, inter alia, by the Adhesiveness & Cohesiveness Test set forth herein.

As used herein, the term "catalytic amount" is a term of the art which is recognized by persons having ordinary skill in the art and refers to an amount that is enough to obtain a desired response or result.

As used herein, the terms "cohesive" and "cohesiveness" refer to the ability of the adhesive component of the present disclosure to retain its structural integrity when subjected to separating or peeling forces. Cohesiveness can be measured, inter alia, by the Adhesiveness & Cohesiveness Test set forth herein. The cohesive attributes can be further reflected by the separation of a medical item attached to the adhesive component without leaving substantially any adhesive component residue upon the surface of the item and by the adhesive component's ability to return to its original innate form upon removal of a medical item attached thereto as prior to attachment of the item.

As used herein, the term "effective amount" refers to the amount required to obtain a desired result.

As used herein, the term "reaction media" refers to a mixture of chemical constituents which, upon curing, forms a releasably adhesive and cohesive viscoelastomeric thermoset polymer component of the present disclosure.

As used herein, the terms "releasable" and "releasability" refer to the setting free from restraint or disengagement of a medical item from the adhesive component, typically by exerting a counteracting force to the item.

As used herein, the terms "viscoelastomeric" and "viscoelastic" can be used interchangeably to refer to a substance having viscous, elastic and flow properties.

These terms may be defined with additional language in the remaining portions of the specification.

DETAILED DESCRIPTION

The invention is generally directed to portable medical stands for presenting medical instruments and supplies, such as Mayo stands, for example. In some more particular embodiments, the present invention relates to medical stands having one or more articulating components for presenting a medical tray member intended for holding medical items during a medical procedure (e.g., a surgical procedure). In some further embodiments, such medical tray can be an adhesive medical tray member comprising an adhesive component disposed thereon. Such inventive articulating medical stands can be useful for, inter alia, positioning the medical tray at an angle that is convenient and/or ergonomic for the user, substantially preventing movement of medical instruments and supplies disposed thereon, maintaining the position/orientation of medical instruments and supplies disposed thereon, preventing medical instruments and supplies from falling off the medical tray even when presented at an angle, reducing the occurrence of dropped items, eliminating the need for additional personnel, etc.

Although several exemplary embodiments of the invention of the present disclosure will be described herein, it should be understood that the disclosed embodiments are intended merely as non-limiting examples of the invention that may be embodied in various forms. Therefore, specific details disclosed herein, such as relating to structure, function, and the like, are not to be interpreted as limiting in any manner whatsoever, but rather only as one of numerous example bases for claims and/or teaching persons having ordinary skill in the art to variously employ the present invention in virtually any appropriately detailed structure or circumstance.

Although the invention of the present disclosure has wide applicability, such as to a medical setting, in the interest of brevity and conciseness, descriptions herein may be substantially directed to the non-limiting exemplary form of an inventive articulating medical stand comprising a vertical support element, a first or bottom horizontal support element, a second or upper horizontal support element, a tray mounting member and an adhesive medical tray member.

To gain a better understanding of the present invention, attention is directed to FIGS. 1-8 for exemplary purposes showing a non-limiting exemplary embodiment of an inventive articulating medical stand 100 of the present disclosure. As illustrated, the articulating medical stand 100 is shown to resemble the non-limiting exemplary form of a Mayo stand.

Referring to FIG. 1, the inventive articulating medical stand 100 comprises a vertical support member 110 having a first or lower end 112 and an opposing second or upper end 114 distal to the lower end 112. The vertical support member 110 provides structural support to the articulating medical stand 100, and helps define the adjustable height of the stand 100, and thus ultimately the height of the adhesive medical tray member 150 for a user. Typically, the adjustable height of the vertical support member 110 can range from a length of about 30 inches (76 cm) to about 60 inches (152 cm). However, it should be understood that the height (i.e., length) of the vertical support member 110 can be less than 30 inches (76 cm) or greater than 60 inches (152 cm) without departing from the scope of the invention. In addition, the lower end 112 can be integral with, or adapted to be attached to, the lower horizontal support member 120, and the upper end 114 can be adapted to be attached to the upper horizontal support member 130. Accordingly, in some preferred embodiments, a housing element 119 (e.g., a cylindrical housing) adapted to receive the first end 132 of the upper horizontal support member 130 can be affixed at or near the upper end 114 of the vertical support member 110.

In some embodiments, the vertical support member 110 can comprise a single component primary structure. In such aspects, the overall height of the inventive articulating medical stand 100 will generally not be adjustable. In some more preferred embodiments, the vertical support member 110 can comprise a multi-component primary structure, such that the overall height of the inventive articulating medical stand 100 can be varied (i.e., vertically adjustable), such as be telescoping, for instance along the longitudinal axis 110, thereof. For example, the vertical support member 110 can comprise a hollow first outer component adapted to accommodate a second inner component which can then telescope within the first outer component (e.g., a core-and-sheath configuration).

In some preferred embodiments, the vertical support member 110 can comprise stainless steel (e.g., 304, 316, etc.) or chrome-plated steel, as such materials can be relatively easily cleaned and sterilized. However, it should be understood that the vertical support member 110 can comprise any suitably functional material that provides adequate vertical support to the articulating medical stand 100 without departing from the scope of the invention, including other metals (e.g., aluminum, titanium, etc.), plastic, fiberglass, wood, and the like.

As referenced above, in some preferred embodiments, the vertical support member 110 can be configured to provide for vertical (i.e., height) adjustment of the articulating medical stand 100. Such vertical adjustment can allow the user to determine (and change as desired) the height of the upper horizontal support member 130 (e.g., as measured from the floor upon which the stand is disposed), and thus ultimately the adhesive medical tray member 150 to conveniently suit a user's particular position (e.g., standing, sitting, leaning, etc.) at any given time. Such vertical length adjustment can be accomplished using any suitable means known to persons having ordinary skill in the art, such as via a telescoping structure, for example. In some preferred embodiments, the vertical support member 110 can alternatively or additionally be configured to provide for axial rotation about its longitudinal axis 110₁. Such axial rotation can allow a user to rotate the upper horizontal support member 130 about the vertical support member 110, and thus ultimately the adhesive medical tray member 150 up to 360° within a horizontal plane to conveniently suit a user's particular position and location at a given time. Such axial rotation can be accomplished using any suitable means known to persons having ordinary skill in the art, such as via a generally cylindrical rod, for example. As illustrated in the non-limiting exemplary embodiment of FIGS. 1-2, both vertical adjustment and axial rotation of the articulating medical stand 100 can be accomplished by utilizing a two-component vertical support member 110 having a core-and-sheath configuration, wherein the sheath portion 110B comprises a generally cylindrical longitudinal opening 110C, and wherein the core portion 110A comprises a rod-like structure and has an outer diameter that is less than the inner diameter of the sheath portion 110B interior opening 110C. For example, the lower end of the sheath portion 110B can be attached to or integral with the lower horizontal support member 120 and the core portion 110A can be disposed within the opening 110C of the sheath portion 110B such that the core portion 110A is moveable (i.e., vertically slidable and/or axially rotatable) with respect to the sheath portion 110B. A cross-section profile of the core portion 110A can have any functional shape known to persons having ordinary skill in the art, such a circular, pentagonal, hexagonal, octagonal, decagonal, etc., without departing from the scope of the invention.

Figure 2:
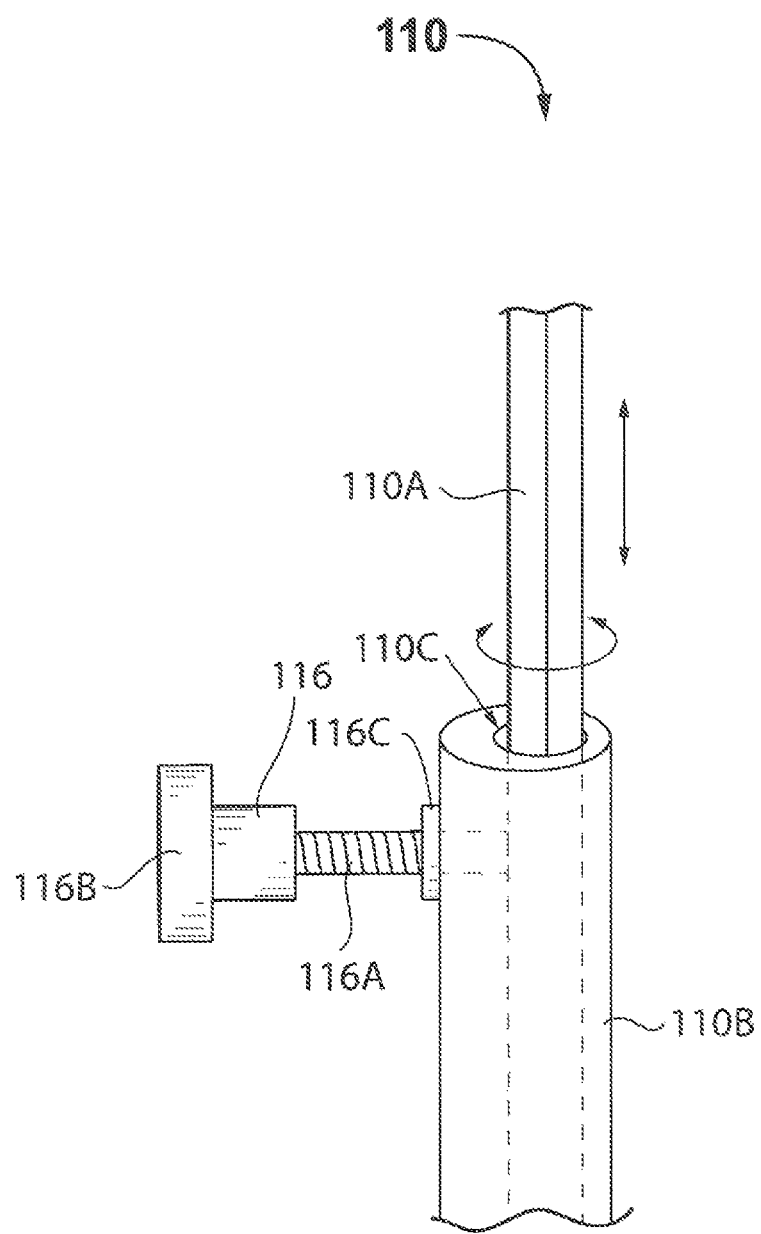
FIG. 2 is a partial perspective view showing a non-limiting exemplary embodiment of a vertical support member.

With particular reference to FIG. 2, in some embodiments, a securing element 116 can be utilized to secure and maintain the vertical support member 110 at a particular height and/or a rotational configuration. Suitable securing elements 116 include any suitable means known to persons having ordinary skill in the art, such as clamps, pressure fittings, screws, pegs, hook-and-loop, and the like. For example, in one non-limiting exemplary embodiment, a threaded rod 116A comprising a knob 116B can be mated with a suitably sized threaded female aperture 116C through the sheath portion 110B of the vertical support member 110, and can be adequately tightened against the core portion 110A (via the knob 116B) to maintain the articulating medical stand 100 at a particular height and/or rotational configuration.

In other embodiments, the vertical support member 110 can be vertically and/or rotationally manipulated automatically (e.g., via electric motors, servos, etc.). Such manipulation may be engaged via connected or remote (e.g., wireless) controllers.

Returning now to FIG. 1, the inventive articulating medical stand 100 also comprises a first or lower horizontal support member 120 having a general bottom side 122 and an opposing general top side 124 distal to the bottom side 122. The lower horizontal support member 120 provides foundational structural support to the articulating medical stand 100 with respect to a floor upon which it is disposed, and helps define the overall stability of the stand 100. In some embodiments, the lower horizontal support member 120 contributes to making the stand 100 portable, and can help determine the ease for which the geographical location of the stand 100 can be manipulated during use.

Typically, the length of the lower horizontal support member 120 will range from about 24 inches (61 cm) to about 36 inches (91 cm). However, it should be understood that the lower horizontal support member 120 can have a length of less than 24 inches (61 cm) or greater than 36 inches (91 cm) without departing from the scope of the invention. In some embodiments (not shown), the length of the lower horizontal support member 120 can be adjustable, such as by telescoping, folding, etc. Such adjustable length can help better accommodate various locations of use (e.g., where space is limited), increase stability when needed, or increase compactness such as for storage of the inventive articulating medical stand 100.

Typically, the lower horizontal support member 120 will comprise the same material of construction as the vertical support member 110, though it need not be. In some preferred embodiments, the lower horizontal support member 120 can comprise stainless steel (e.g., 304, 316, etc.) or chrome-plated steel, as such materials are relatively strong, and can be relatively easily cleaned and sterilized. However, it should be understood that the lower horizontal support member 120 can comprise any suitably functional material that provides adequate base support to the articulating medical stand 100 without departing from the scope of the invention, including other metals (e.g., aluminum, titanium, etc.), plastic, fiberglass, wood, and the like, and combinations thereof. In addition, the lower horizontal support member 120 can have any functional shape profile without departing from the scope of the invention, including rectangular, square, circular, ovular, trapezoidal, star-shaped, etc. Furthermore, the lower horizontal support member 120 can be linear or nonlinear, can have a uniform or non-uniform profile, and can be solid or hollow, without departing from the scope of the invention.

As referenced above, the lower end 112 of the vertical support member 110 can be attached to or integral with the lower horizontal support member 120, typically upon the top side 124 thereof, and typically at a location approximating the center thereof. However, it should be understood that other locations can also be suitable without departing from the scope of the invention. In the case where the vertical support member 110 is attached to (as opposed to integral with) the lower horizontal support member 120, such attachment can be made using any suitable means known to persons having ordinary skill in the art, such as welding, bolts, screws, clamps, adhesives, and the like, or combinations thereof. In some embodiments, it may be desirable that an attached vertical support member 110 can be detachable (and re-attachable) to help assist with cleaning or storing the stand 100.

Figure 3:
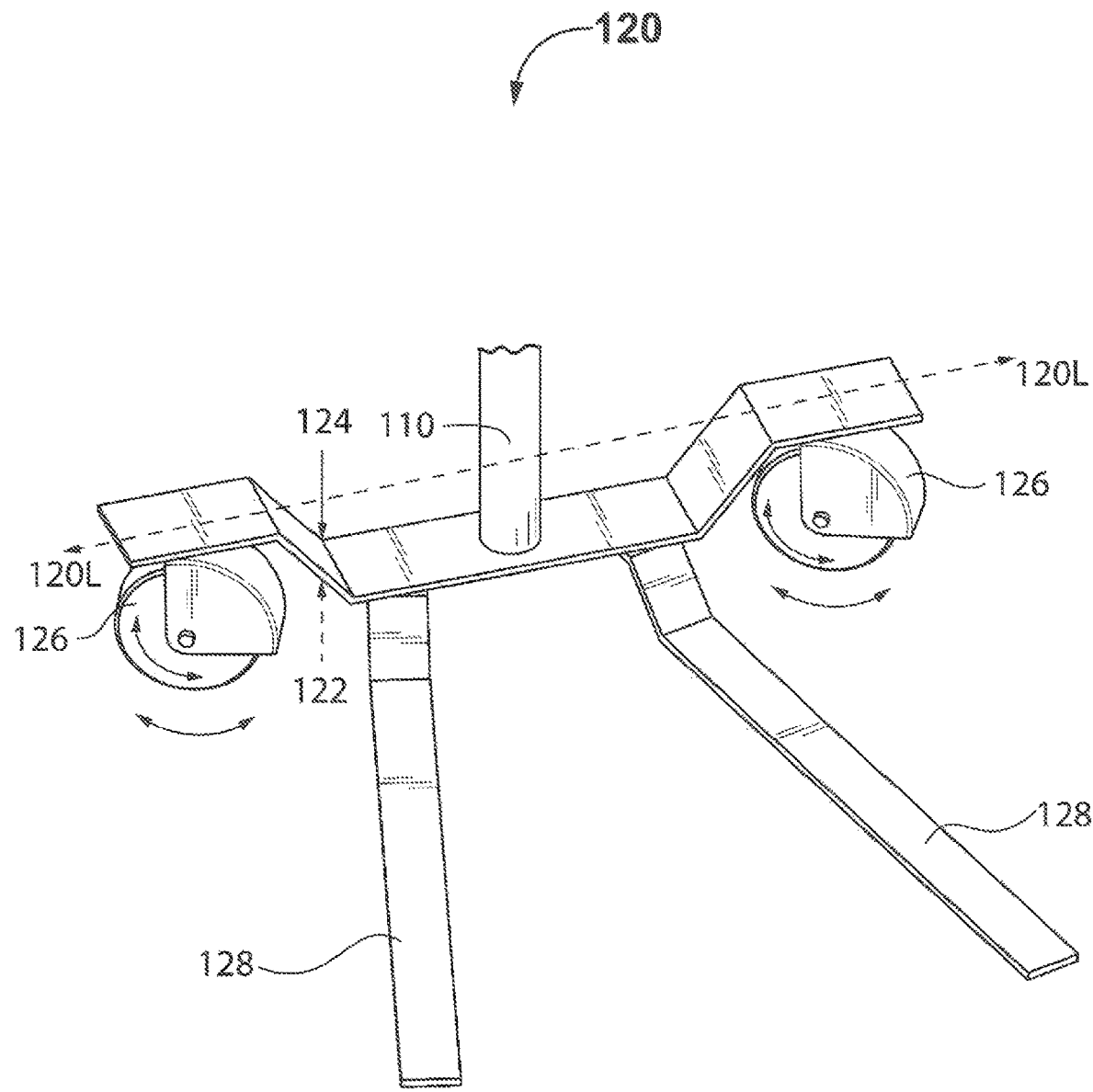
FIG. 3 is a perspective view showing a non-limiting exemplary embodiment of a lower horizontal support member.
Figure 4A:
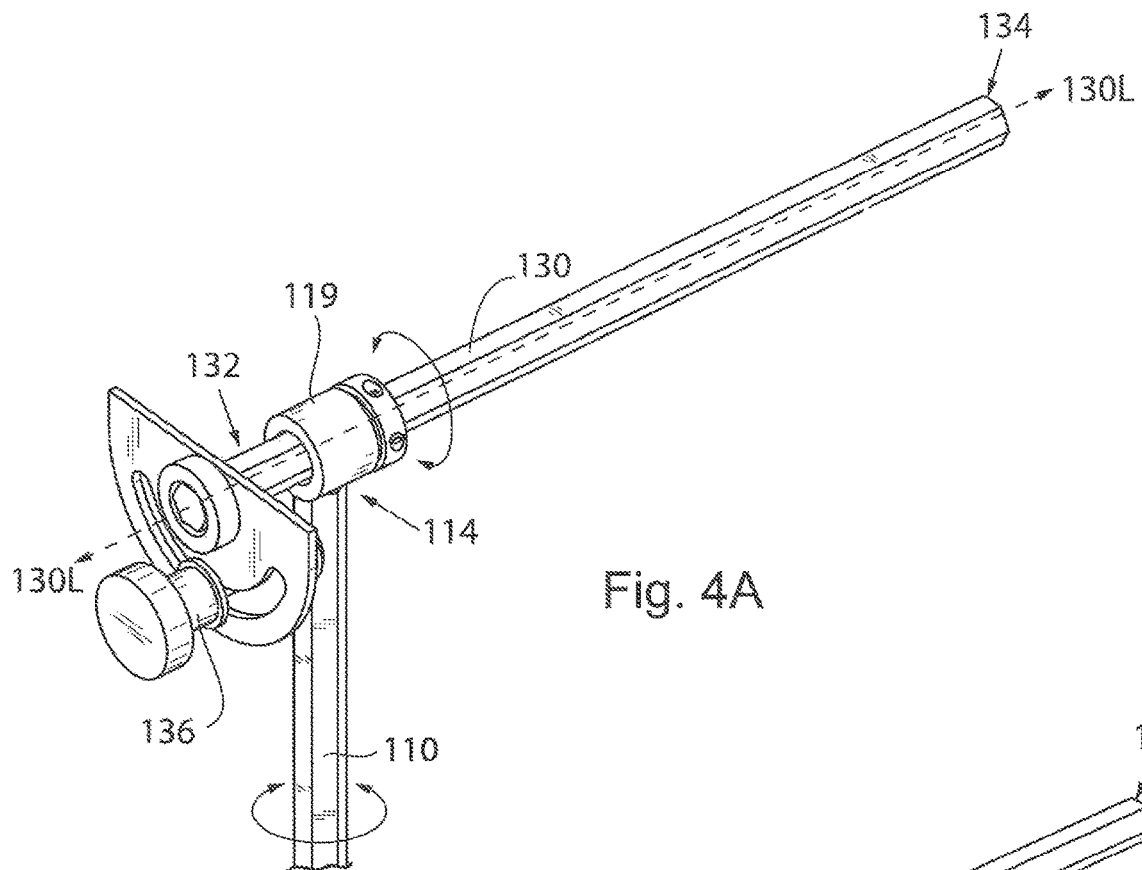
FIG. 4A is a perspective view showing a non-limiting exemplary embodiment of an upper horizontal support member.
Figure 4B:
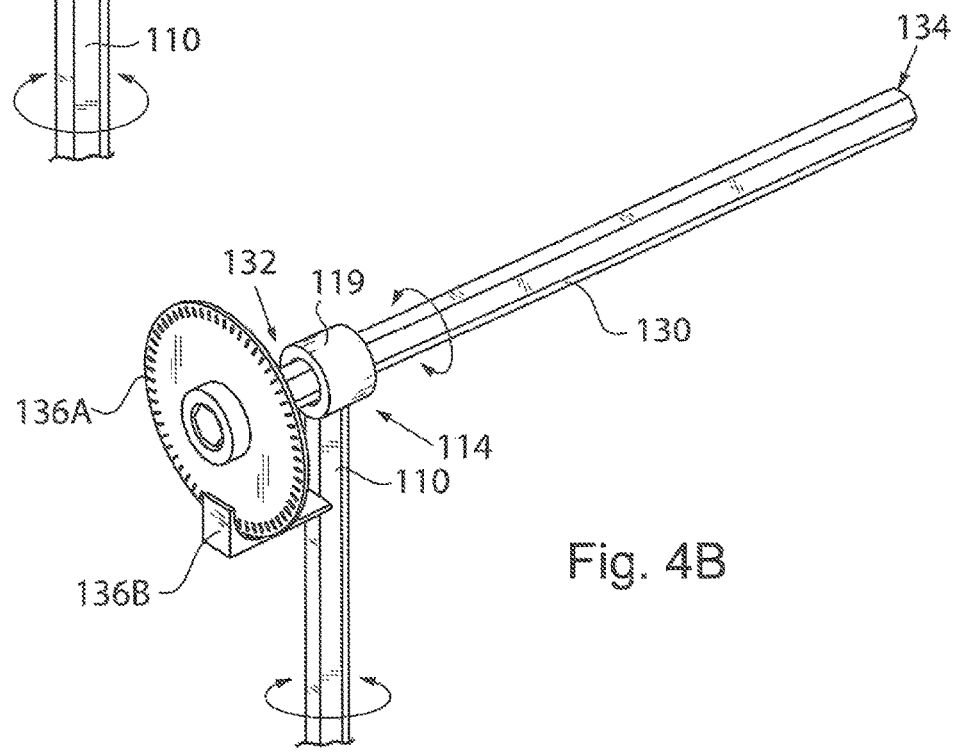
FIG. 4B is a perspective view showing a non-limiting exemplary embodiment of an upper horizontal support member comprising a securing member in the form of a notched disk element.

With additional reference to FIG. 3, in some preferred embodiments, the bottom side 122 of the lower horizontal support member 120 will desirably comprise at least one maneuvering member 126, and more preferably at least two maneuvering members, attached thereto. Such maneuvering members 126 can assist with rendering the inventive articulating medical stand 100 to be more portable, and can further assist with geographical repositioning of the stand 100 during use. Suitable maneuvering members 126 can include those known to persons having ordinary skill in the art, and can include castors, balls, wheels, cylindrical rollers, and the like, or combinations thereof. In some preferred embodiments, swivel castors can be utilized as the maneuvering members 126 (see e.g., FIG. 3).

Continuing with FIGS. 1-3, in some preferred embodiments, the lower horizontal support member 120 can further comprise at least one protruding stability support member 128, which can be disposed upon the floor when the inventive articulating medical stand 100 is at rest, and which can be lifted off the floor (e.g., by levering back the stand 100) during times of moving or repositioning the stand 100. Such stability support member 128 can help prevent the articulating medical stand 100 from tipping over, such as when downward pressure is applied to the adhesive medical tray member 150 by a user when removing or replacing a medical item 180 (i.e., medical instrument or supply), for example. Typically, at least one stability support member 128 will extend generally laterally from the lower horizontal support member 120 (i.e., laterally from the longitudinal axis 120, thereof). However, it need not be precisely perpendicular to the longitudinal axis 120, of the lower horizontal support member 120. Indeed, since the upper horizontal support member 130 of the inventive articulating medical stand 100 possesses the unique ability to axially rotate about the vertical support member 110, it may be desirable that such stability support members 128 extend from the lower horizontal support member 120 at an angle (e.g., other than 90° from the longitudinal axis 120L, such as an outward-facing angle) from the longitudinal axis 120, to provide additional support in multiple directions (see e.g., FIG. 3 showing a general "V" shape of the illustrated stability support members 128).

Typically, the length of the stability support member(s) 128 will be about 24 inches (61 cm) to about 36 inches (91 cm). However, it should be understood that each stability support member 128 can have a length of less than 24 inches (61 cm) or greater than 36 inches (91 cm) without departing from the scope of the invention. In some embodiments (not shown), the length of the stability support member 128 can be adjustable, such as by telescoping, folding, etc., without departing from the scope of the invention.

Typically, the stability support member(s) 128 will comprise the same material of construction as the lower horizontal support member 120, though it need not be. In some preferred embodiments, the stability support members 128 can comprise stainless steel (e.g., 304, 316, etc.) or chrome-plated steel, as such materials are relatively strong, and can be relatively easily cleaned and sterilized. However, it should be understood that the stability support member 128 can comprise any suitably functional material that provides adequate support for the weight of the articulating medical stand 100 without departing from the scope of the invention, including other metals (e.g., aluminum, titanium, steel, etc.), plastic, fiberglass, wood, and the like, and combinations thereof. In addition, the stability support member 128 can have any functional cross-sectional shape profile without departing from the scope of the invention, including rectangular, square, circular, ovular, trapezoidal, star-shaped, etc. Furthermore, the stability support members 128 can be linear or nonlinear, can have a uniform or non-uniform profile, and can be solid or hollow, without departing from the scope of the invention.

In some embodiments, the bottom side of the stability support member 128 can optionally comprise a coating (not shown) or a pad element (not shown) disposed thereon, typically near the distal end thereof, which can provide additional grip and/or cushioning (e.g., rubber, silicone, felt, etc.) when the stand 100 is at rest. In other embodiments, the stability support member 128 can comprise a rolling member (not shown), such as a locking caster, which can improve portability of the inventive articulating medical stand 100, while also allowing for suitable anchoring of the stand 100 during use.

In further embodiments, it may be desirable to include one or more additional stability support members (not shown), which may be of shorter length, at other locations around the periphery of the lower horizontal support member 120. Such additional stability support members can provide further stability (e.g., prevention from tipping over) to the inventive articulating medical stand 100, particularly when rotation of the upper horizontal support member 130 (via the vertical support member 110) has occurred. Typically, such additional stability support members will be disposed slightly higher than the primary stability support member 128, such as between about 1 mm to about 10 mm above the floor when the stand 100 is at rest, to allow for levering or leaning the stand 100 such as during the portability (e.g., geographical repositioning) of the stand 100. Accordingly, such embodiments of the invention could experience a slight rocking of the stand while rotating the upper horizontal support member 130 about the vertical support member 110, but will prevent the stand 100 from completely falling over.

Returning now to FIG. 1, the inventive articulating medical stand 100 also comprises an upper horizontal support member 130 having a first end 132 and an opposing second end 134 distal to the first end 132. The upper horizontal support member 130 provides, inter alia, structural support for the tray mounting member 140 and the adhesive medical tray member 150, including when the tray mounting member 140 and the adhesive medical tray member 150 are manipulated, such as during use. In addition, the upper horizontal support member 130 can be repositioned, such as via axial rotation about its longitudinal axis 130L. Such axial rotational adjustment functionality allows a user to position the presentation of medical items 180 (i.e., medical instruments and supplies) at a convenient usable and/or ergonomic location during use (without the need for an additional medical professional to "hand-off" the items 180 to the user), and further allows the user to reposition the location of the adhesive medical tray member 150 comprising items 180 during use, which provides a significant advantage over existing conventional medical stands (e.g., Mayo stands) which at most allow for height adjustment only, and which typically require an additional medical professional to provide the items 180 from such conventional medical stands to the user.

Typically, the length of the upper horizontal support member 130 will be about 24 inches (61 cm) to about 36 inches (91 cm). However, it should be understood that the length of the upper horizontal support member 130 can be less than 24 inches (61 cm) or greater than 36 inches (91 cm) without departing from the scope of the invention. In some embodiments, it may be desirable that the length of the upper horizontal support member 130 and the length of each stability support member 128 will be substantially similar (e.g., with minor variation of +/−5 inches), though they need not be.

In some embodiments, the upper horizontal support member 130 can have a generally linear cylindrical shape profile, which can allow for axial rotation thereof. The outer diameter of such an upper horizontal support member 130 design is not critical (and will depend at least partly upon the material and construction of the member 130), provided it can suitably support the tray mounting member 140 and the adhesive medical tray member 150, including when the tray mounting member 140 and the adhesive medical tray member 150 are manipulated. Accordingly, the outer diameter of the upper horizontal support member 130 (which may be solid or hollow) will typically range from about 0.25 inches (0.6 cm) to about 3 inches (8 cm). However, it should be understood that the outer diameter of the upper horizontal support member 130 can be less than 0.25 inches (0.6 cm) or greater than 3 inches (8 cm) without departing from the scope of the invention. It should also be understood that a cross-section profile of the upper horizontal support member 130 can have any functional shape known to persons having ordinary skill in the art, such a circular, pentagonal, hexagonal, octagonal, decagonal, etc., without departing from the scope of the invention.

Typically, the upper horizontal support member 130 will comprise the same material of construction as the vertical support member 110, though it need not be. In some preferred embodiments, the upper horizontal support member 130 can comprise stainless steel (e.g., 304, 316, etc.) or chrome-plated steel, as such materials can be relatively easily cleaned and sterilized. However, it should be understood that the upper horizontal support member 130 can comprise any suitably functional material that provides adequate support to the tray mounting member 140 and the adhesive medical tray member 150 components of the inventive articulating medical stand 100 without departing from the scope of the invention, including other metals (e.g., aluminum, titanium, etc.), plastic, fiberglass, wood, and the like, and combinations thereof.

In some preferred embodiments, the general first end 132 portion of the upper horizontal support member 130 can be rotatably connected at or proximate to the upper end 114 of the vertical support member 110 via the housing member 119 disposed thereon. More particularly, and with additional reference to FIGS. 4A-4B, in some embodiments, the general first end 132 portion of the upper horizontal support member 130 can be disposed through the housing member 119. A securing member 136 (e.g., a tensioning securing member) can be utilized to maintain an axially rotated position of the upper horizontal support member 130. Suitable securing members 136 include any suitable means known to persons having ordinary skill in the art, such as clamps, pressure fittings, screws, pegs, hook-and-loop, and the like. In some embodiments, the securing member can be similar to that described above for the vertical support member 110 (see e.g., FIG. 4A). However, it should be understood that other suitable securing members as are known to persons having ordinary skill in the art can also be utilized. For example, in one non-limiting exemplary embodiment, a dimpled disk element 136A affixed to the first end 132 of the upper horizontal support member 130 can be mated with a suitable fastening element 136B which is affixed at or proximate to the upper end 114 of the vertical support member 110, such that the upper horizontal support member 130 can be clicked into a particular rotatable position and maintained at such position until intentionally changed by a user (see e.g., FIG. 4B). In other embodiments, the upper horizontal support member 130 can be rotated automatically (e.g., via electric motors, servos, etc.). Such manipulation may be engaged via connected or remote (e.g., wireless) controllers.

Figure 5:
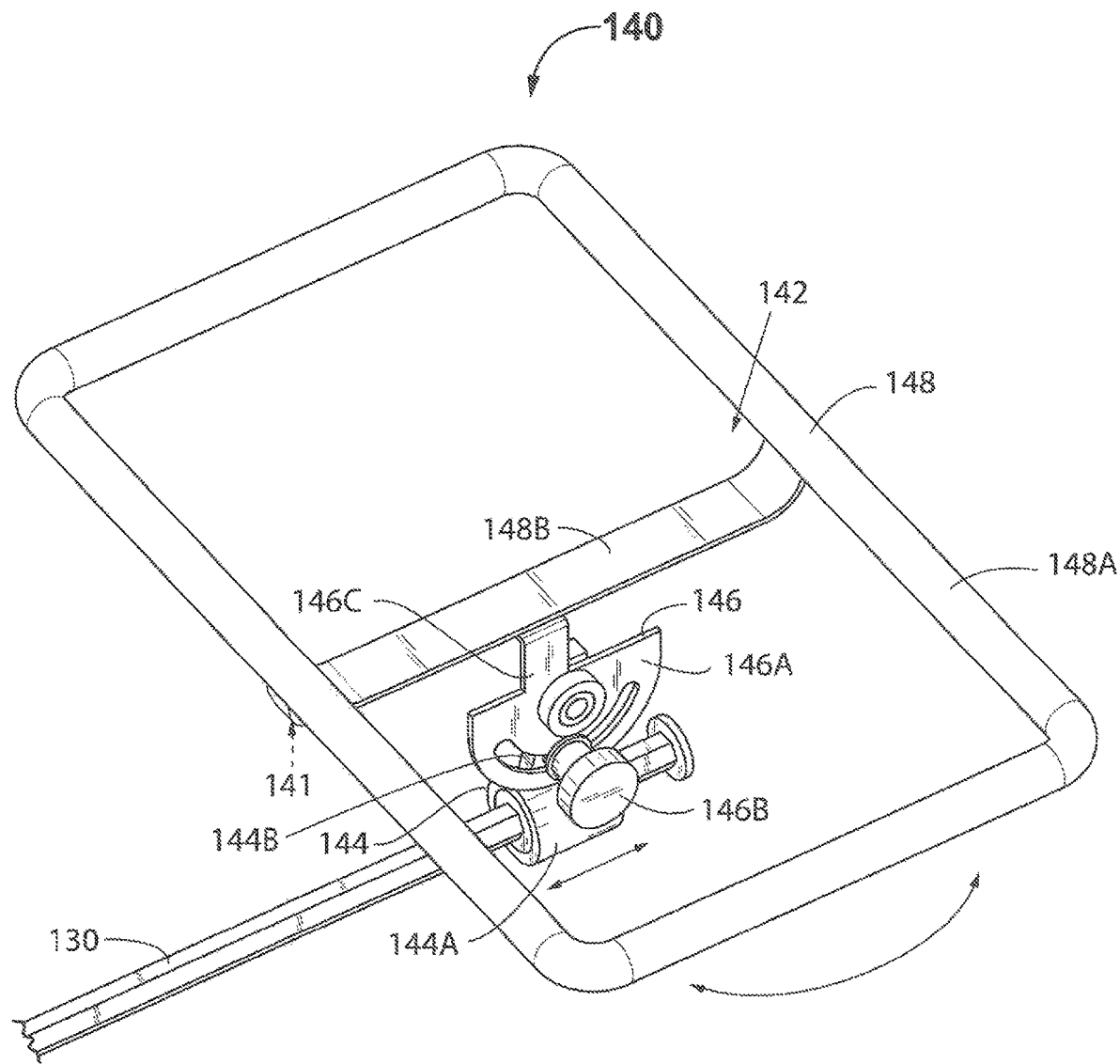
FIG. 5 is a perspective view showing a non-limiting exemplary embodiment of a tray mounting member.

Returning now to FIG. 1, and with additional reference to FIG. 5, the inventive articulating medical stand 100 also comprises a tray mounting member 140 having a general first or bottom side 141 and an opposing general second or top side 142 distal to the bottom side 141. The tray mounting member 140 provides, inter alia, structural support and attachment functionality for the adhesive medical tray member 150, including when the medical stand 100 is manipulated, such as during use. In some preferred embodiments, the tray mounting member 140 can be angularly repositioned with respect to the longitudinal axis 130L of the upper horizontal support member 130 via angular rotation by way of an adjustable connector element 146. In addition, the entire tray mounting member 140 (and thus the adhesive medical tray member 150 disposed thereon) can be further repositioned linearly along the longitudinal length $130_X$ of the upper horizontal support member 130 via a housing support element 144. Such adjustment functionality allows a user to position the presentation of medical items 180 at a convenient usable location during use virtually without limits (and without the need for an additional medical professional to hand-off the items 180 to the user), and further allows the user to reposition the location of the adhesive medical tray member 150 during use, which provides a significant advantage over existing conventional medical stands (e.g., Mayo stands) which at most allow for height adjustment only, and which typically require an additional medical professional to provide the items 180 from such conventional stands to the user. Accordingly, in some preferred embodiments, the tray mounting member 140 comprises a housing support element 144, a tray receiving element 148 and an adjustable connector element 146 disposed therebetween.

As illustrated in the non-limiting exemplary embodiment shown in FIG. 5, the housing support element 144 can comprise a housing component 144A and a support base component 144B attached to or integral with the upper end or top side of the housing component 144A. Preferably, the housing component 144A is adapted to slideably mate with the upper horizontal support member 130 such that the tray mounting member 140 can rotate in tandem with the upper horizontal support member 130 while also having the capability to be linearly repositioned along the longitudinal length $130_X$ of the upper horizontal support member 130, preferably with some resistance. Preferably, the housing support element 144 is adapted to receive the adjustable connector element 148, such as by comprising a threaded female receptacle (not shown), for example. It should be understood that any suitable component for receiving the adjustable connector element 148 as is known to persons having ordinary skill in the art can be utilized without departing from the scope of the invention. Typically, the housing support element 144 will comprise the same material of construction as the upper horizontal support member 130, though it need not be. In some aspects, the housing support element 144 can comprise stainless steel (e.g., 304, 316, etc.) or chrome-plated steel, as such materials can be relatively easily cleaned and sterilized. However, it should be understood that the housing support element 144 can comprise any suitably functional material that provides adequate support and functionality without departing from the scope of the invention, including other metals (e.g., aluminum, titanium, etc.), plastic, fiberglass, wood, and the like, and combinations thereof.

Continuing with the illustrated non-limiting exemplary embodiment shown in FIG. 5, the tray mounting member 140 also comprises an adjustable connector element 146. The purpose of the adjustable connector element 146 is to provide interconnection between the housing support element 144 and the tray receiving element 148, and can further provide for angular rotational adjustment of the tray receiving element 148 (e.g., with respect to the longitudinal axis 130, of the upper horizontal support member 130). For example, in some aspects, the adjustable connector element 146 can comprise an adjustment component 146A which can allow for angular adjustment of the tray receiving element 146 of up to about 360°, such as up to about 180°, or up to about 90°, for example. The adjustable connector element 146 can also comprise a set component 146B (e.g., a threaded knob, a clamp, a set screw, etc.) which can maintain a particular angular setting, as well as can allow for adjustment of the angular setting. In other embodiments, the tray mounting member 140 can be angularly adjusted automatically (e.g., via electric motors, servos, etc.). Such manipulation may be engaged via connected or remote (e.g., wireless) controllers.

In some preferred embodiments, the adjustable connector element 146 can also comprise a support component 146C located proximate to or upon the top side of the adjustable connector element 146 to which the tray receiving element 148 can be attached. However, it should be understood that the adjustable connector element 146 can comprise any suitable connector as is known to persons having ordinary skill in the art that can connect and support the tray receiving element 148 while also providing for angular movement of the tray receiving element 148, such as a ball-and-socket, a "snake" connector, and the like, without departing from the scope of the invention. Typically, the adjustable connector element 146 will comprise the same material of construction as the upper horizontal support member 130, though it need not be. In some aspects, the adjustable connector element 146 can comprise stainless steel (e.g., 304, 316, etc.) or chrome-plated steel, as such materials can be relatively easily cleaned and sterilized. However, it should be understood that the adjustable connector element 146 can comprise any suitably functional material that provides adequate support and functionality for the tray receiving element 148 without departing from the scope of the invention, including other metals (e.g., aluminum, titanium, etc.), plastic, fiberglass, wood, and the like, and combinations thereof.

Continuing with the illustrated non-limiting exemplary embodiment shown in FIG. 5, the tray mounting member 140 also comprises a tray receiving element 148, which is attached to or interconnected with the adjustable connector element 146. The purpose of the tray receiving element 148 is to secure (e.g., releasably secure) and support an adhesive medical tray member 150, such that the adhesive medical tray member 150 remains connected to the inventive articulating medical stand 100 until intentionally removed. This functionality is important when repositioning the articulating medical stand 100, such as rotating the adhesive medical tray member 150 via the upper horizontal support member 130 and/or angling the adhesive medical tray member 150 via the tray mounting member 140. Indeed, it would be highly undesirable for the adhesive medical tray member 150 to dislodge from the articulating medical stand 100 during a medical procedure (e.g., surgery). In some embodiments, the tray receiving element 148 can comprise a frame component 148A which can substantially mimic the shape and dimensions of an adhesive medical tray member 150 intended to be utilized. Accordingly, the inner dimensions of the frame component 148A can be generally equal to the outer dimensions of the adhesive medical tray member 150 (excluding the lip 156, if present). For example, in some embodiments, the frame component 148A can comprise a generally unitary structure constructed of a fairly rigid cylindrical or tubular material (which may be solid or hollow), such as stainless steel (e.g., 304, 316, etc.), chrome-plated steel, other metals (e.g., aluminum, titanium, etc.), plastic, fiberglass, wood, and the like, and combinations thereof. Typically, the diameter of the material will range from about 0.25 inches (6 mm) to about 1 inch (25 mm), although the material can have a diameter of less than 0.25 inches (6 mm) or greater than 1 inch (25 mm) without departing from the scope of the invention. Such a construction can allow the adhesive medical tray member 150 to be "snapped" into the frame component 148A, thus utilizing tension and/or friction to secure the adhesive medical tray member 150 to the articulating medical stand 100 until a sufficient counteracting force is applied by a user to dislodge the tray 150 from frame component 148A of the articulating medical stand 100. It should be understood that other structures as would be apparent to persons having ordinary skill in the art that are suitable for releasably securing the adhesive medical tray member 150 to the articulating medical stand 100 can also be utilized without departing from the scope of the invention, including the additional use of releasable adhesives. In the case of utilizing releasable adhesive, the dimensions of the frame component 148A with respect to the dimensions of the adhesive medical tray member 150 can become less of a factor for consideration.

In some embodiments, it may be desirable to include an optional crossbeam support component 148B upon the tray receiving element 148, which can extend from one distal end of the frame component 148A to another, for example. Such a crossbeam support component 148B can, inter alia, provide additional structural support to the frame component 148A, and can also provide additional support to the adhesive medical tray member 150 when installed. In addition, such a crossbeam support component 148B can provide an alternative location for attachment of the tray receiving element 148 to the adjustable connector element 146 (as opposed to attaching a portion of the frame component 148A to the adjustable connector element 146). As a result, the tray receiving element 148 can be more centered (i.e., less offset) with respect to the upper horizontal support member 130 than when a location of the frame component 148A is directly connected to the adjustable connector element 146. Typically the crossbeam support component 148B will be constructed of the same material as the frame component 148A, though it need not be. Accordingly, the crossbeam support component 148B can comprise any suitable fairly rigid material (compatible with the frame component 148A material) as is known to persons having ordinary skill in the art, including stainless steel (e.g., 304, 316, etc.), chrome-plated steel, other metals (e.g., aluminum, titanium, etc.), plastic, fiberglass, wood, and the like, and combinations thereof. In the case, such as described above, where at least a portion of the adhesive medical tray member 150 is inserted into the frame component 148A, it may be desirable to configure the crossbeam support component 148B such that it can accommodate such inserted portion of the adhesive medical tray member 150. For example, the crossbeam support component 148B can be configured to have a stretched "U" shape, such as shown in the non-limiting illustrated example of FIG. 5, wherein the majority of crossbeam support component 148B is elevationally offset with respect to the frame component 148A, thus providing depth to the tray receiving element 148. More particularly, the lower portion of the "U" shape can be extensively flat (though it need not be) with the end portions curving towards the frame component 148A (e.g., curving upwards when the frame component 148A is facing upwards). Accordingly, the distal end portions of the crossbeam support component 148B will typically be affixed to distal portions of the frame component 148A. Any suitable, preferably permanent, attachment means known to persons having ordinary skill in the art can be utilized without departing from the scope of the invention, including welding, screws, bolts, adhesives, and the like, and combinations thereof.

Figure 6A:
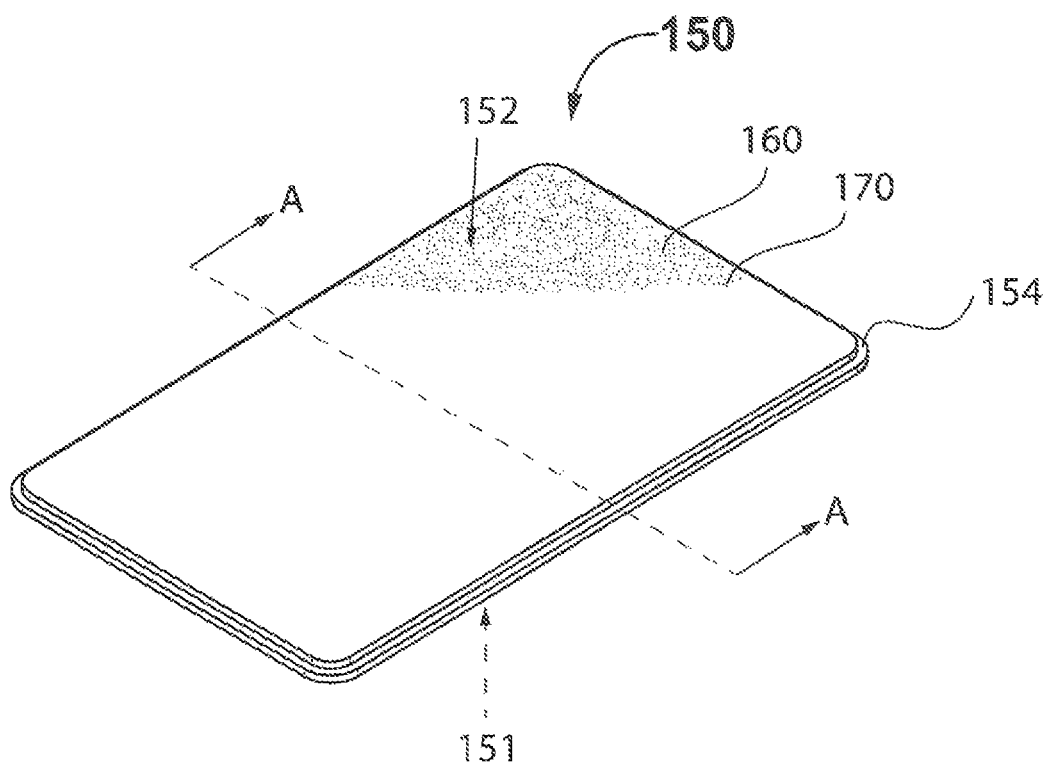
FIG. 6A is a perspective view showing a non-limiting exemplary embodiment of an adhesive medical tray member.
Figure 6B:
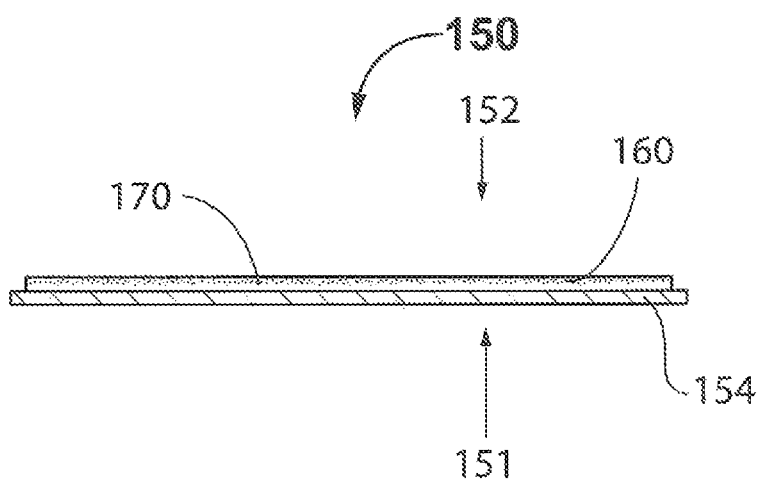
FIG. 6B is a side view of the adhesive medical tray member of FIG. 6A as taken along line A-A.
Figure 7A:
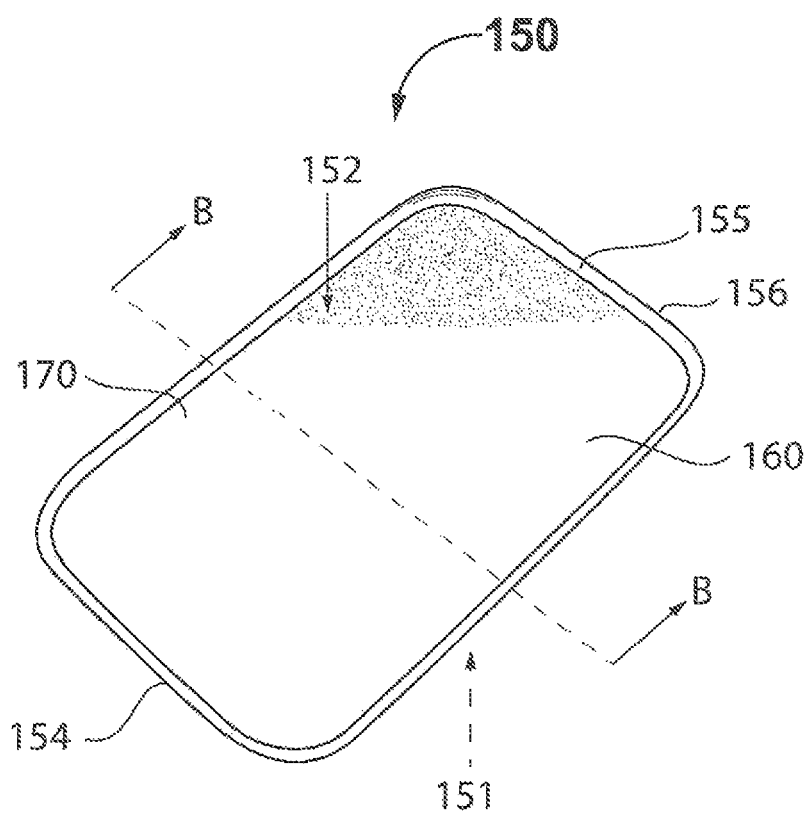
FIG. 7A is a perspective view showing a non-limiting exemplary embodiment of an adhesive medical tray member comprising an optional side element and an optional lip element.
Figure 7B:
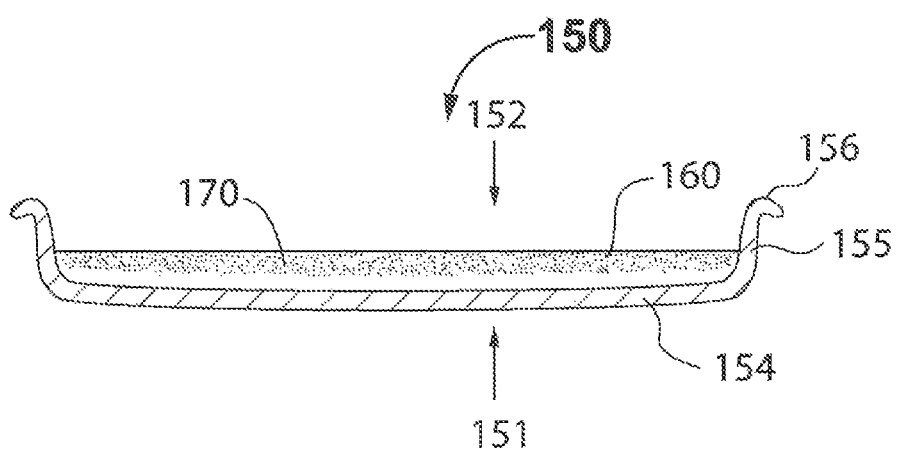
FIG. 7B is a side view of the adhesive medical tray member of FIG. 7A as taken along line B-B.
Figure 7C:
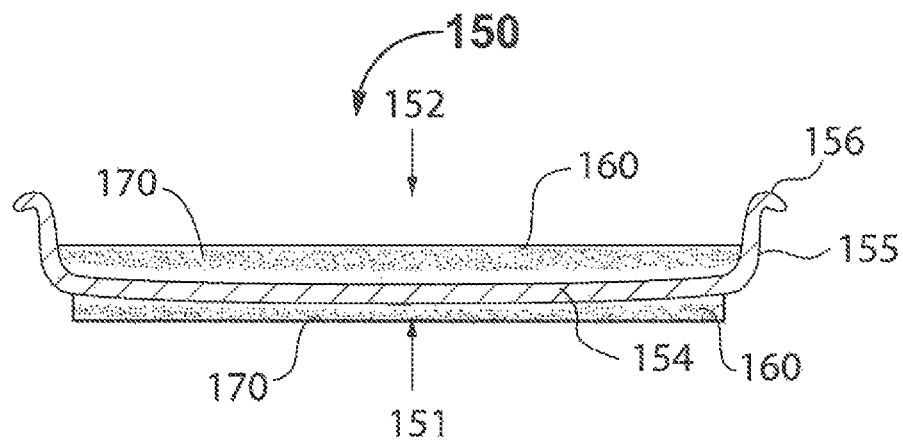
FIG. 7C is a side view of an alternative embodiment of the adhesive medical tray member of FIG. 7A as taken along line B-B comprising an additional adhesive component disposed upon the bottom side thereof.
Figure 7D:
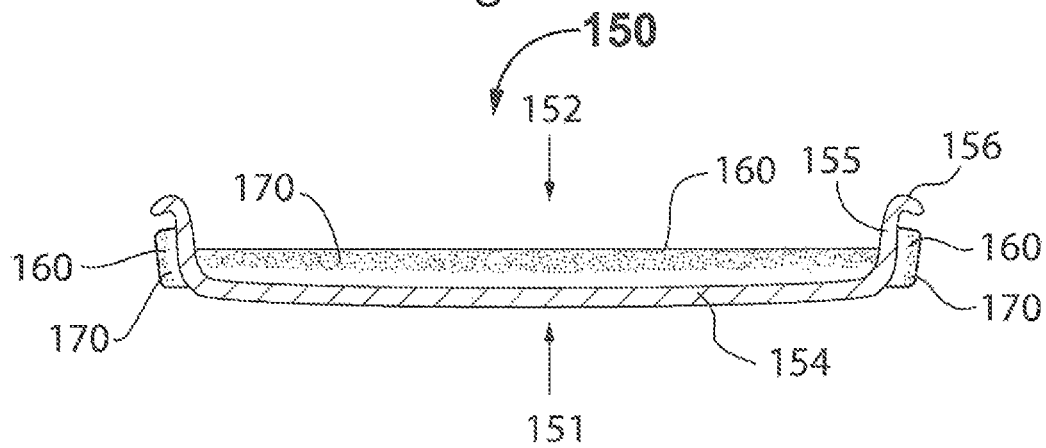
Fig. 7D is a side view of an alternative embodiment of the adhesive medical tray member of FIG. 7A as taken along line B-B comprising additional adhesive components disposed upon the optional side elements.
Figure 7E:
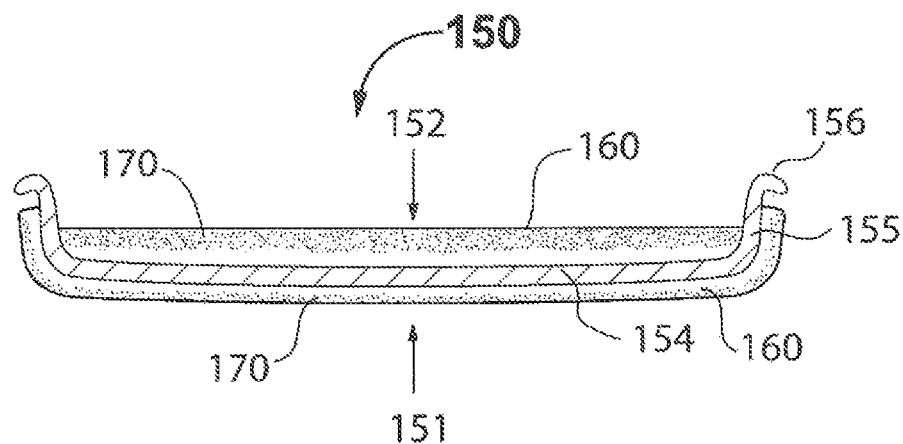
FIG. 7E is a side view of an alternative embodiment of the adhesive medical tray member of FIG. 7A as taken along line B-B comprising an additional adhesive component disposed upon the bottom side thereof and upon the optional side elements.

Returning now to FIG. 1, and with additional reference to FIGS. 6A-6B, the inventive articulating medical stand 100 also comprises a novel adhesive medical tray member 150. The purpose of the adhesive medical tray member 150 is to provide a location for placement of various medical items 180 to be used during a medical procedure, and to releasably secure such medical items 180 thereto, even when the adhesive medical tray member 150 is angularly rotated up to 360°. The unique adhesive medical tray member 150 comprises a tray component 154 and an adhesive component 160, such as a releasably adhesive and cohesive viscoelastomeric thermoset polymer component 170 (which may also be more simply referred to herein as the "polymer component 170"), for example.

The tray component 154 of the adhesive medical tray member 150 can have a platform-like configuration, comprising a first or bottom planar side 151 and an opposing second or top planar side 152 distal to the bottom planar side 151. Typically, the tray component 154 will comprise stainless steel (e.g., 304, 316, etc.) or chrome-plated steel, as such materials are relatively strong, and can be relatively easily cleaned and sterilized. However, it should be understood that tray component 154 can comprise any suitably functional material known to persons having ordinary skill in the art which is fairly rigid and that provides adequate support to the medical items 180 placed thereupon without departing from the scope of the invention, including other metals (e.g., aluminum, titanium, etc.), plastic, tempered glass, plexiglass, wood, and the like, and combinations thereof.

The tray component 154 will typically have a general rectangular shape (e.g., when viewing the top side 152), which is a fairly standard shape for trays in the medical field. However, it should be understood that the tray component 154 can have any functional shape without departing from the scope of the invention, including square, circular, ovular, trapezoidal, etc. Typically, the tray component 154 will have size dimensions that are generally equivalent to the dimensions of the tray receiving element 148 of the inventive articulating medical stand 100, though it need not be. Indeed, the tray component 154 is not limited to any particular dimensions, provided it can be suitably affixed to the tray receiving element 148.

With additional reference to FIGS. 7A-7E, in some aspects, the tray component 154 can further comprise an optional side element 155 which may disposed vertically or at an angle at least partially around the perimeter of the tray component 154. Such optional side element 155 can assist with attachment to certain styles of tray receiving elements 148 (e.g., frame-like tray receiving elements 148), and can provide three-dimensional depth to the adhesive medical tray member 150, if so desired. In some additional aspects, the tray component 154 can further comprise an optional lip element 156 which may be disposed along the upper edge of the optional side element 155, for example. Such optional lip element 156 can be useful for assisting a user with grasping the adhesive medical tray member 150, and can also be useful where the adhesive medical tray member 150 is intended to "snap" into the tray receiving element 148, such as in the non-limiting example described above.

In addition to the tray component 154, the adhesive medical tray member 150 also comprises an adhesive component 160 disposed at least partially upon the top side 158 of the tray component 154. Any suitable releasable adhesive as is known to persons having ordinary skill in the art can be utilized as the adhesive component 160 without departing from the scope of the invention. In some preferred embodiments, the adhesive component 160 can preferably be in the form of an inventive releasably adhesive and cohesive viscoelastomeric thermoset polymer component 170. Such polymer component 170 (which may be colorless or color tinted) will typically have a thickness of about 0.02 inch (0.5 mm) to about 0.5 inch (13 mm), such as about 0.04 inch (1 mm) to about 0.25 inch (6 mm). However, it should be understood that the polymer component 170 can be disposed upon the tray component 154 at a suitable thickness of less than 0.02 inch (0.5 mm) or greater than 0.5 inch (13 mm) without departing from the scope of the invention.

The unique releasably adhesive and cohesive viscoelastomeric thermoset polymer component 170 can typically be formed via the preparation and subsequent curing of a thermosetting reaction media. In some preferred embodiments, the reaction media comprises (based on the total reaction media weight) about 2 percent by weight (wt %) to about 10 wt % isocyanate prepolymer, about 35 wt % to about 75 wt % polyols comprising about 1 wt % to about 65 wt % (based on the total reaction media weight) straight chain linking polyols and about 3 wt % to about 50 wt % (based on the total reaction media weight) crosslinking polyols, and about 10 wt % to about 60 wt % plasticizer comprising about 10 wt % to less than about 45 wt % (based on the total reaction media weight) epoxidized triglyceride plasticizer and about 0 wt % to about 40 wt % (based on the total reaction media weight) viscosity-reducing plasticizer, preferably an ester plasticizer. Desirably, the polymer is formed from a substantially uniform admixture of the reaction media constituents.

It has been discovered herein that the reaction media and the resulting polymer component 170 are substantially free from VOC's. It has been further discovered herein that the weight of the reaction media and the weight of the resulting polymer component 170 (i.e., upon curing the reaction media) remain substantially constant. Thus, the "wt %" values of each component referenced above can alternatively be expressed in terms of total "polymer" weight, without departing from the scope of the invention. Accordingly, in some preferred embodiments, the releasably adhesive and cohesive viscoelastomeric thermoset polymer component 170 comprises (based on the total polymer weight) about 2 wt % to about 10 wt % isocyanate prepolymer, about 35 wt % to about 75 wt % polyols comprising about 1 wt % to about 65 wt % (based on the total polymer weight) straight chain linking polyols and about 3 wt % to about 50 wt % (based on the total polymer weight) crosslinking polyols, and about 10 wt % to about 60 wt % total plasticizer comprising about 10 wt % to less than about 45 wt % (based on the total polymer weight) epoxidized triglyceride plasticizer and about 0 wt % to about 40 wt % (based on the total polymer weight) viscosity-reducing plasticizer, preferably an ester plasticizer. Of course, it should be understood that when expressing the components in terms of wt % based on total "polymer" weight, such components have actually been combined and reacted to form the polymer thereof. In the interest of brevity, the "wt %" of the polymer constituents will typically be expressed in terms of total reaction media weight herein.

In some embodiments, the straight chain polyols and the crosslinking polyols can each comprise repetitive oxygen groups. In other embodiments, the straight chain polyols and the crosslinking polyols can each comprise repetitive ether groups. In still other embodiments, the straight chain polyols and the crosslinking polyols can each comprise hydroxyl groups, desirably wherein two (2) of the hydroxyl groups are terminal hydroxyl groups. In some preferred embodiments, the straight chain polyols and the crosslinking polyols can each comprise a polyether having a molecular weight of about 1,000 to about 20,000, such as about 1,000 to about 10,000, or about 1,000 to about 8,000 for improved benefits. In some embodiments, the straight chain polyols and crosslinking polyols can be present in a straight chain polyol to crosslinking polyol weight ratio of about 1:3 to about 3:1.

In some embodiments, the plasticizer is uniformly dispersed and cohesively bound throughout the polymeric infrastructure of the polymer component 170. In some embodiments, the polymer component 170 can comprise an epoxidized triglyceride plasticizer to viscosity-reducing plasticizer weight ratio of 1:0 to about 1:3.

The releasably adhesive and cohesive viscoelastomeric thermoset polymer component 170 of the present invention is particularly well suited for use with the adhesive medical tray member 150 of the inventive articulating medical stand 100, such as the non-limiting exemplary embodiments described herein. As referenced above, such unique polymer component 170 can comprise an isocyanate prepolymer, polyols in the form of straight chain polyols (e.g., diols) and crosslinking polyols (e.g., triols or higher), and select plasticizers. The isocyanate prepolymer in combination with prescribed amounts of straight chain polyols and crosslinking polyols provides a thermoset infrastructure for effectively housing the plasticizer(s) in a form which unexpectedly contributes to unique viscoelastomeric, cohesiveness, adhesiveness, releasability, cleansability, reusability and antimicrobial features of the polymer component 170. Furthermore, the unexpected cohesiveness attributes of the polymer component 170 provides for a stabilized polymer which exhibits substantially no plasticizer leakage (also referred to as "bleeding") despite the relatively high plasticizer content (i.e., about 10 wt % or greater).

As referenced above, the releasably adhesive and cohesive viscoelastomeric thermoset polymer component 170 can be derived from a thermosetting reaction media comprised of a substantially uniform admixture of an isocyanate prepolymer, prescribed amounts of polyols (e.g., polyether diols and polyether triols) and a carefully controlled amount of select plasticizers. The isocyanate prepolymer in combination with a controlled amount of polyols in the form of straight chain polyols (preferably diols) and crosslinking polyols (preferably crosslinking triols) provides a thermoset infrastructure for effectively housing the plasticizing components in a form which unexpectedly contributes to the unique stabilized, viscoelastic, adhesive, cohesive, releasability and antimicrobial attributes of the adhesive medical tray member 150, while also permitting a restorative cleansability function via conventional washing and/or autoclaving techniques. Accordingly, the unexpected cohesiveness attributes of the polymer component 170 substantially prevent plasticizer leakage, which solves a long-standing problem of existing polymers having high plasticizer loadings (i.e., having a plasticizer content of greater than about 10 wt % of the total reaction media weight).

A highly effective thermosetting reaction media for preparing the releasably adhesive and cohesive viscoelastomeric thermoset polymer component 170 of the present disclosure comprises a prepolymer, polyols and plasticizer. More particularly, the reaction media comprises (i) a prepolymer, such as an isocyanate prepolymer (e.g., a polyol reacted with an isocyanate), more preferably a diisocyanate prepolymer (e.g., methylene diphenyl diisocyanate (MDI)), ranging from about 2 wt % to about 10 wt % of the total reaction media weight; (ii) polyols, ranging from about 35 wt % to about 75 wt % of the total reaction media weight, wherein the polyols include straight chain linking polyols (preferably diols) and crosslinking polyols (preferably triols); and (iii) plasticizer, ranging from about 10 wt % to about 60 wt % of the total reaction media weight, wherein the plasticizer includes an epoxidized triglyceride plasticizer in an amount of about 10 wt % to less than about 50 wt % of the total reaction media weight, such as about 10 wt % to less than about 45 wt % of the total reaction media weight to provide improved benefits, and optionally a reaction media viscosity-reducing plasticizer, preferably an ester plasticizer, in an amount of about 0 wt % to about 40 wt % of the total reaction media weight. The polymer component 170 can also optionally comprise additional components including, but not limited to, additional plasticizers, catalysts, initiators, colorants (e.g., dyes), UV inhibitors, antioxidants, and the like, as would be known to persons having ordinary skill in the art, without departing from the scope of the invention. As referenced above, it has been observed herein that the weight of the reaction media and the weight of the resulting reaction product (i.e., the polymer component 170) remains substantially equivalent upon mixing and curing the reaction media; thus, the compositional amount (i.e., wt %) of each constituent may be expressed in terms of "wt % by weight of the polymer" without departing from the scope of the invention.

As referenced above, the thermosetting reaction media (and thus the resulting polymer component 170) comprises a quantity of prepolymer which forms the backbone of the releasably adhesive and cohesive viscoelastomeric thermoset polymer component 170. Such prepolymer will typically be present in an amount of about 2 wt % to about 10 wt % of the total reaction media weight, such as about 3 wt % to about 9 wt %, or about 4 wt % to about 8 wt % of the total reaction media weight to provide improved benefits. Suitable prepolymers can include a ring-opening species of a hardener (e.g., amines, amides, mercaptans, anhydrides, isocyanates including polyisocyanates (such as a diisocyanate), etc.). Suitable polyisocyanates include, but are not limited to, aromatic diisocyanates (e.g., diphenylmethane diisocyanate, methylene diphenyl diisocyanate (MDI), toluene diisocyanate (TDI), etc.) and aliphatic diisocyanates (e.g., hexamethylene diisocyanate (HDI), isophorone diisocyanate (IPDI), etc.) in a conventional prepolymer form. In one non-limiting example, a methylene diphenyl diisocyanate (MDI) designated as ELASTOCAST TQZ-P23, available from BASF Corporation, having a place of business located in Florham Park, New Jersey, USA, can provide a suitable prepolymer to form the polymer component 170 of the inventive articulating medical stand 100.

The thermosetting reaction media (and thus the resulting inventive articulating medical stand 100) also comprises a quantity of polyols, typically ranging from about 35 wt % to about 75 wt % of the total reaction media weight, such as about 38 wt % to about 65 wt %, or about 40 wt % to about 55 wt % of the total reaction media weight, to provide improved benefits. More particularly, the polyols include straight chain polyols and crosslinking polyols. In some desirable aspects, the straight chain polyols can be in the form of diols (e.g., a diol having two terminal reactive groups), and the crosslinking polyols can be in the form of triols (e.g., having two terminal reactive groups and one additional reactive group). In such aspects, the diol and triol components of the reaction media are typically liquid at room temperature (i.e., about 21° C.) and generally have a molecular weight of about 1,000 to about 20,000, such as about 1,000 to about 15,000, or about 1,000 to about 10,000, to provide improved benefits. The adhesiveness and cohesiveness of the resulting releasably adhesive and cohesive viscoelastomeric thermoset polymer component 170 depend upon using a controlled polyol balance within the thermosetting reaction media. It has been discovered herein that the amount of diols and triols (preferably reacted in the presence of an effective amount of plasticizer within the reaction media) can suitably fall within a prescribed diol to triol weight ratio of about 1:3 to about 3:1, such as about 1:2 to 2:1, or about 7:13 to about 13:7, to provide the desired viscoelastic, adhesive, cohesive, releasability, cleansability, and/or antimicrobial (including antipathogenic) attributes for effective use herein (while also inhibiting plasticizer leakage from the polymer component 170). The content and type of polyols can have a pronounced effect upon imparting the necessary thermoset polymeric infrastructure for obtaining the polymer component 170 attributes herein. Accordingly, it has been discovered herein that when the weight ratio of diols to triols deviates outside a range of about 1:3 to about 3:1, the desired adhesiveness, cohesiveness and releasability attributes of the resultant polymer will begin to diminish. Thus, controlled amounts within the cited ranges with respect to the straight chain diols and the crosslinking triols can provide an effective reaction media for preparing a polymer component 170 uniquely possessing the viscoelastic, adhesiveness, cohesiveness, releasability, cleansability, and antimicrobial features for the adhesive medical tray member 150. It has also been discovered herein that the resulting polymer component 170 further possesses a resistance to melting when subjected to heat.

In general, the straight chain polyol component of the releasably adhesive and cohesive viscoelastomeric thermoset polymer component 170 can provide straight chain infrastructure formation and sufficient crosslinkage disruption to permit for a highly effective intermolecular plasticizer attraction and alignment, thus providing for an unusually high and effective loading of the viscoelastic, adhesive, cohesive and antipathogenic contributing plasticizer cofactors. In some preferred embodiments, the straight chain polyol can be provided by a polyether diol having a molecular weight suitably ranging from about 1,000 to about 10,000, such as about 1,000 to about 8,000, or about 2,000 to about 6,000 for improved benefits, and preferably having two (2) terminal reactive groups (e.g., hydroxyl groups). Such polyether diol can be suitably present in an amount ranging from about 1 wt % to about 65 wt % of the total reaction media weight, such as about 5 wt % to about 55 wt %, or about 10 wt % to about 45 wt % of the total reaction media weight, to provide improved benefits. In one example, a 2-functional polyether diol, designated as ELASTOCAST C-4057, available from BASF Corporation, can provide a suitable straight chain polyol component to form the polymer component 170 of the inventive articulating medical stand 100.

In general, the crosslinking polyol component of the releasably adhesive and cohesive viscoelastomeric thermoset polymer component 170 can provide sufficient crosslinkage infrastructure to the polymer component 170, and can contribute to the unexpected cohesiveness, releasability and stability (i.e., inhibiting plasticizer leakage) attributes thereof. In some preferred embodiments, the crosslinking polyol can be provided by a polyether triol having a molecular weight suitably ranging from about 1,000 to about 10,000, such as about 2,000 to about 8,000, or about 3,000 to about 7,000 for improved benefits, and preferably having three (3) reactive groups (e.g., hydroxyl groups, wherein two (2) of the reactive groups are terminal reactive groups). Such polyether triol can be suitably present in an amount ranging from about 3 wt % to about 50 wt % of the total reaction media weight, such as about 10 wt % to about 45 wt %, or about 20 wt % to about 40 wt % of the total reaction media weight, to provide improved benefits. In one example, a 3-functional polyether triol, designated as ELASTOCAST C-4018, available from BASF Corporation, can provide a suitable triol component to form the polymer component 170 of the inventive articulating medical stand 100.

The adhesiveness properties of the polymer component 170 can be tailored to fit the need for any given medical items 180 to be attached to the adhesive medical tray member 150 of the inventive articulating medical stand 100. Accordingly, the thermosetting reaction media may be properly formulated so as to impart a desired degree of adhesiveness for the adherence and stabilization of any given medical item 180 adhered to the adhesive medical tray member 150 while still retaining the desired cohesiveness of the polymer component 170. For example, in general, increasing the straight chain polyol to crosslinking polyol weight ratio (e.g., increasing the diol content relative to the triol content) will result in an increased adhesiveness of the polymer component 170. Conversely, decreasing the straight chain polyol to crosslinking polyol weight ratio (e.g., increasing the triol content relative to the diol content) will generally result in a decreased adhesiveness and an increased cohesiveness of the polymer component 170. Thus, controlling the straight chain polyol to crosslinking polyol weight ratio within the range of about 3:1 to about 1:3 for example can result in a polymer component 170 having a desired adhesiveness and cohesiveness for the adhesion and subsequent release of any particular medical item 180.

The releasably adhesive and cohesive viscoelastomeric thermoset polymer component 170 also comprises a total quantity of plasticizer(s) typically ranging from about 10 wt % to about 60 wt % of the total reaction media weight, such as about 15 wt % to about 55 wt %, or about 20 wt % to about 50 wt % of the total reaction media weight, to provide improved benefits. More particularly, the plasticizer components include a triglyceride plasticizer, and can optionally further include a process aid (i.e., reaction media viscosity-reducing) plasticizer. In preferred embodiments, the triglyceride plasticizer is an epoxidized triglyceride plasticizer, and the optional viscosity-reducing plasticizer is an ester plasticizer. The plasticizer components of the thermoset reaction media are typically liquid at room temperature (i.e., about 21° C.). It has been discovered herein that the weight ratio of triglyceride plasticizer to viscosity-reducing plasticizer can suitably fall within a weight ratio range of about 1:0 to about 1:1, such as about 6:1 to about 1:3, or about 3:1 to about 1:2, to provide a workable reaction media viscosity for a particular application, and to help provide the desired viscoelasticity, adhesiveness, cohesiveness, releasability, cleansability, and/or antipathogenic attributes of the resulting polymer component 170. The content and type of plasticizers can have a pronounced effect upon imparting the desired polymer component 170 attributes herein. Thus, a controlled amount of triglyceride plasticizer (e.g., epoxidized triglyceride plasticizer) and optional viscosity-reducing plasticizer (e.g., ester plasticizer) within the prescribed range can provide an effective reaction media for preparing a polymer component 170 uniquely possessing the desired compositional attributes for use herein. Desirably, the plasticizer components are uniformly dispersed and cohesively bound throughout the thermosetting reaction media (along with the other polymerizable thermosetting components) and will tenaciously remain uniformly dispersed within the resultant polymer component 170 in a highly cohesive and stabilized (i.e., resistance to plasticizer leakage) form.

Suitable triglyceride plasticizers for preparing the releasably adhesive and cohesive viscoelastomeric thermoset polymer component 170 desirably include epoxidized triglyceride plasticizers. Epoxidized triglyceride plasticizers, such as epoxidized animal oils and epoxidized vegetable oils, are particularly effective as a plasticizer component in the thermosetting viscoelastomeric reaction media herein. Amongst the suitable epoxidized triglyceride plasticizers, epoxidized vegetable oils (e.g., soybean, corn, cottonseed, perilla, safflower, linseed, tall, etc.) have been found to be particularly effective triglyceride plasticizers herein. Other suitable triglyceride plasticizers have been more extensively described in the aforementioned cross-referenced related applications. Such triglyceride plasticizers can be suitably present in an amount of 0 wt % to about 50 wt % of the total reaction media weight, such as about 1 wt % to about 45 wt %, or about 10 wt % to less than about 45 wt % of the total reaction media weight, to provide improved benefits. In one desirable example, epoxidized soybean oil can provide a highly suitable triglyceride plasticizer to form the polymer component 170 of the adhesive medical tray member 150.

As referenced above, the releasably adhesive and cohesive viscoelastomeric thermoset polymer component 170 can also optionally comprise a suitable reaction media viscosity-reducing plasticizer. In general, those plasticizers which are suitable as plasticizing agents for the plasticization of polyvinyl chlorides can be utilized as viscosity-reducing plasticizers for the reaction media herein. Exemplary viscosity-reducing plasticizers for preparing the polymer component 170 can include, but are not limited to, ester plasticizers. Such ester plasticizers are especially effective as an optional additional plasticizer component in the thermosetting reaction media. Suitable ester plasticizers typically have a relatively low molecular weight (typically less than about 750, or less than about 500) and can include, but are not limited to, the condensation products of alcohols (e.g., $C_1$-$C_{10}$ alcohols, such as $C_2$-$C_6$ alcohols) and dicarboxylic acids (e.g., $C_2$-$C_{12}$ dicarboxylic acids, such as $C_4$-$C_8$ dicarboxylic acids). In addition, amongst the more fluid ester plasticizers, such as diester plasticizers for example, are the lower dialkyl esters of dicarboxylic acids, such as dialkyl esters having alkyl groupings of less than 12 carbon atoms, such as $C_1$-$C_8$ dialkyl ester groupings of sebacates, adipates, phthalates, isophthalates, maleates, azelates, glutarates, etc., which have been found to be particularly effective ester plasticizers herein.

In some aspects, the polar strength (often referred to as "dipole moment") of such ester plasticizers depends, to a certain degree, upon the alcohol condensation reactant chain length, which can also have an effect upon the adhesiveness characteristics of the thermoset viscoelastomeric reaction product (i.e., the polymer component 170). For example, non-epoxidized plasticizers having a relatively high dipole moment (e.g., dibutyl sebacate, having a dipole moment of 2.48 debyes (D), as compared to epoxidized plasticizers having a dipole moment near 0 D) can be effective in retaining the desired properties of the polymerizate while also providing a thermosetting reaction media exhibiting a reduced working viscosity, if such is desired for a particular fabrication process. Suitable ester plasticizers can have a dipole moment of greater than about 1.5 D, such as greater than about 2.0 D, to provide improved benefits. The ester plasticizers can be suitably present in an amount ranging from about 0 wt % to about 40 wt % of the total reaction media weight, such as about 1 wt % to about 30 wt %, or about 2 wt % to about 20 wt % of the total reaction media weight for improved benefits in certain applications. In one non-limiting example, dibutyl sebacate can provide a highly suitable optional ester plasticizer when forming the reaction media of the present disclosure.

In some aspects, the incorporation (preferably within the ranges prescribed herein) of the relatively low molecular weight ester plasticizer in combination with the triglyceride plasticizer (e.g., epoxidized triglyceride plasticizer) can be utilized herein to provide an easier fabricating form (e.g., for casting, molding, injecting, pouring, spraying, printing, etc.) of the uncured polymer mix (i.e., reaction media) by lowering the viscosity of the reaction media without adversely affecting the desirable features of the releasably adhesive and cohesive viscoelastomeric thermoset polymer component 170. For example, the addition of polar ester plasticizers, or substitution of the triglyceride plasticizers with polar ester plasticizers, has been found to effectively reduce the viscosity of the reaction media while still maintaining a desired level of adhesiveness and cohesiveness of the resulting polymer component 170, as well as maintaining excellent releasability and stability properties. It has been discovered herein that including an ester plasticizer having a fluidic consistency at room temperature (i.e., about 21° C.) and having a relatively low molecular weight (e.g., less than about 750) in the reaction media can contribute to ideal working viscosities during the initial curing stages, rendering the reaction media to be more workable (e.g., from a viscosity standpoint) when forming the adhesive medical tray member 150 of the inventive articulating medical stand 100.

As referenced above, the plasticizer component is desirably uniformly incorporated into the thermosetting reaction media (along with the other polymerizable thermosetting reactants) and will tenaciously remain uniformly dispersed within the resultant polymer component 170 in a highly cohesive and stabilized form. The straight chain polyols and crosslinking polyols, in cooperative combination with the plasticizer, create a viscoelastic thermoset polymeric structure possessing a suitable degree of compositional cohesiveness and releasable adhesiveness which is desirable to adhesively secure and retain medical items 180, while also allowing for a clean cohesive separation of the medical items 180 from the adhesive medical tray member 150 (upon application of a sufficient counteracting force to the medical items 180 which overcomes the adhesive force of the polymer component 170), desirably leaving no visually detectable polymeric residue on the medical items 180, and more preferably leaving no polymeric residue on the medical items 180 whatsoever. Controlling the reaction media weight ratio of triglyceride plasticizer and optional ester plasticizer (along with the straight chain polyol to crosslinking polyol weight ratios) accordingly constitutes an important consideration in preparing the reaction media for the releasably adhesive and cohesive viscoelastomeric thermoset polymer component 170. For example, if the amount of plasticizer is excessively high (i.e., outside the range prescribed herein), the resultant polymer component 170 will tend to lose its desired cohesiveness and will then tend to permanently distort (i.e., may not return to its original innate form as when initially formed), and/or will tend to leak plasticizer. However, it has been discovered herein that in certain instances, increasing the crosslinking polyol content can partially arrest such plasticizer leakage, but such an increase in crosslinking polyol content will then tend to decrease the adhesiveness of the polymer component 170.

The unique bridged crosslinked polymeric structure (e.g., crosslinking triols separated by straight chain diols) of the thermoset polymerizate 170 obtained from an appropriate thermoset reaction media provides an ideal infrastructure for effectively harboring the plasticizer in an unexpectedly superior cohesive and adhesive form. Indeed, it appears that the crosslinked infrastructure and the polarity provided by the polymerized straight chain polyols and crosslinking polyols orients the polarized plasticizer within the resulting polymer component 170 so as to impart, inter alia, the unexpected viscoelasticity, adhesiveness, releasability, cohesiveness, stability, cleansability and antimicrobial properties to the polymer component 170 herein.

The releasably adhesive and cohesive viscoelastomeric thermoset polymer component 170 can also optionally comprise additional constituents including, but not limited to, catalysts, initiators, other additional plasticizers, colorants, UV inhibitors, antioxidants, and the like, as would be known to persons having ordinary skill in the art, without departing from the scope of the invention. For example, the polymerization of the thermosetting reaction media can be carried out in the presence of a catalyzing amount (defined above) of a catalyst (e.g., a slow-acting catalyst or a heat-activated catalyst) to control the curing rate of the reaction media. Suitable catalysts can include tertiary amines, tertiary phosphines, strong bases (e.g., alkali, alkaline earth metal hydroxides, alkoxides, phenoxides, etc.), acidic metal salts of strong acids, metal chelates, metal alcoholates, metal phenolates, organic acid salts, organo metallic derivatives, etc. In one non-limiting example, COSCAT 83 (available from Vertellus Holdings LLC, having a place of business located in Zeeland, Michigan, USA), which is a slow-acting organobismuth catalyst, can provide a suitable catalyst for controlling the curing rate of the thermosetting reaction media to form the polymer component 170. In another non-limiting example, FOMREZ CATALYST UL-29 (available from Momentive Performance Materials Inc., having a place of business located in Wilton, Connecticut, USA), which is a heat-activated tin thioglycolate catalyst, can provide a suitable catalyst for controlling the curing rate of the thermosetting reaction media to form the polymer component 170.

Procedurally, the reaction product which forms the releasably adhesive and cohesive viscoelastomeric thermoset polymer component 170 can be prepared from a thermosetting reaction media homogeneously loaded with plasticizer (s) which includes a triglyceride plasticizer (preferably an epoxidized triglyceride plasticizer, such as epoxidized vegetable oil) as well as optionally any other effective polar plasticizer, coupled with a carefully measured amount of straight chain polyols (e.g., diols) and crosslinking polyols (e.g., triols) to create the necessary bridging between the crosslinks, and an isocyanate prepolymer hardener (e.g., diisocyanate, such as aliphatic, aromatic, heterocyclic, etc., polyisocyanates, cycloaliphatic isocyanates and arylaliphatic isocyanates), and typically in the presence of an appropriate catalyst (e.g., preferably a relatively slow-acting catalyst). The reaction media desirably contains the necessary plasticizer loading specifically adapted to provide a curable reaction media, which upon curing, produces a viscoelastomeric reaction product (i.e., the polymer component 170) having a unique polymerizate structure effectively loaded with polar oriented plasticizers uniformly and homogeneously distributed throughout the polymer's entire thermoset mass, intertwined therewithin, and supported by the flexible plasticizer-entrapping thermoset polymerizate structure. Under the most effective thermosetting and fabricating conditions, the thermosetting polymerizate reactants and the plasticizers are collectively provided in the reaction media as liquids at room temperature (i.e., about 21° C.) without necessitating the use of any solvents, other chemical dispersion aids or elevated temperatures, in order to homogeneously disperse the reaction media components. Accordingly, this allows the thermosetting reaction to be effectively conducted at room temperature.

The crosslinked polymeric structure of the releasably adhesive and cohesive viscoelastomeric thermoset polymer component 170 obtained from an appropriate thermosetting reaction media provides an ideal infrastructure for effectively harboring plasticizer components in an unexpectedly desirable viscoelastic, releasably adhesive, cohesive and stabilized polymeric form, while also providing unexpected antimicrobial properties and cleansability/reusability properties, as well as a resistance to melting when subjected to heat. As referenced above, the plasticizer is uniformly incorporated throughout the reaction media containing the polymerizable components, and remains uniformly dispersed within the resultant polymer component 170 in a highly cohesive form, thus preventing leakage of the plasticizers therefrom. It appears that the crosslinked infrastructure and the polarity provided by the polymerized straight chain polyols (e.g., polyether diols) and crosslinking polyols (e.g., polyether triols) orients the polarized plasticizer components (e.g., epoxidized triglyceride plasticizer and optional ester plasticizer) within the resulting polymer component 170 to impart the unexpected viscoelasticity, adhesiveness, cohesiveness, releasability, stability, cleansability, reusability and antimicrobial properties to the adhesive medical tray member 150 of the inventive articulating medical stand 100. Thus, the thermosetting straight chain polyols and crosslinking polyols in cooperative combination with the plasticizer create a thermoset polymeric structure possessing a high degree of compositional adhesiveness and cohesiveness for effective usage with the inventive articulating medical stand 100 of the present disclosure, while also allowing for a clean cohesive separation of medical items 180 from the adhesive medical tray member 150 (i.e., leaving essentially no polymeric residue on any surface of the medical items 180).

From a molecular infrastructure standpoint, the unique combination of straight chain and crosslinking reactants and plasticizer types in the amounts prescribed herein creates a uniquely different polymer component 170. The appropriate control of straight chain polyol and crosslinking polyol reactants appears to create long chain polarized sites ideal for powerful cohesive polar entrapment of the plasticizer(s) while also aligning the polarized plasticizer components in a powerful adhesive and cohesive positioning within the polymer component 170. The polarized molecular alignment of the plasticizer cofactor within the polymeric infrastructure contributes to a highly cohesive structure which maintains its molecular integrity when subjected to forces which effect separation of the polymer component 170 from a contacting surface of a medical item 180, which can be critical during a medical procedure (such as a surgical procedure). The plasticizer appears to also be a major contributing factor in the polymer's unique viscoelastomeric properties. As a result, the polymer component 170 possesses a host of unexpectedly unique and superior properties (e.g., adhesiveness, cohesiveness, releasability, stability, cleansability, reusability, antimicrobial, etc.) over conventional adhesive polymers currently available.

As referenced above, the thermoset prepolymer (e.g., isocyanate prepolymer), the straight chain linking polyols (e.g., diols) and the crosslinking polyols (e.g., triols), in cooperative combination with the plasticizer(s), create a polymer component 170 having antimicrobial properties, as well as a thermoset viscoelastic polymeric structure possessing a high degree of compositional adhesiveness and cohesiveness necessary to adhesively secure and retain medical items 180, in addition to a clean cohesive separation from the medical items' 180 surfaces. The type of plasticizers and reactants described herein in controlled amounts (i.e., within the quantity ranges prescribed herein) can also be effectively utilized to provide desirable thermosetting fabrication conditions for preparing the polymer component 170, and thereby providing unique adhesive medical tray members 150 possessing the unique attributes herein, which thus contributes to the functionality of the inventive articulating medical stand 100.

As a result of its unique chemical composition and processing conditions, the releasably adhesive and cohesive viscoelastomeric thermoset polymer component 170 of the adhesive medical tray members 150 herein possesses a host of unique and unexpected properties. For example, the polymer component 170 exhibits advantageously unique viscoelastic properties. Due to its fluidic attributes (as opposed to compression properties, such as found in foam or rubber compositions), such viscoelastic properties allow the polymer component 170 to at least partially surround and conform to the configuration of a medical item 180 due to the weight of such item 180 and/or force exerted when a user places the item 180 upon the adhesive medical tray member 150. The result is an increased contacting surface area of the medical items 180 for better adhesion and adhesive performance. This provides a significant advantage over conventional adhesive products (which typically exhibit compression properties as opposed to viscoelastic properties).

In addition, the polymer component 170 of the adhesive medical tray member 150 herein also exhibits advantageously unique releasable adhesiveness properties. The overall tackiness or adhesiveness of the polymer component 170 and its concomitant releasability characteristics can be effectively altered so as to match the needs of a particular medical item 180 by changing the compositional makeup of the thermosetting reaction media, particularly the straight chain polyol to crosslinking polyol reaction media weight ratio, as well as the reaction media plasticizer content and the types of plasticizers. For example, an increase in the amount of straight chain polyol (with respect to the amount of crosslinking polyol) will tend to increase the adhesiveness of the polymer component 170, and thus also increase the amount of force required to release a medical item 180 from the adhesive medical tray member 150. Conversely, an increase in the amount of crosslinking polyol (with respect to the amount of straight chain polyol) will tend to decrease the adhesiveness of the polymer component 170, and thus also decrease the amount of force required to release a medical item 180 from the adhesive medical tray member 150. In the case where the amount of straight chain polyol (with respect to the amount of crosslinking polyol) is increased, it has been found herein that a slight increase in the amount of prepolymer will generally serve to balance the reaction media reactants. In general, adhesive medical tray members 150 having a relatively high degree of adhesiveness will tend to be less effective for releasing relatively small, light and/or fragile medical items 180, but will tend to be more effective for adhering and stabilizing relatively larger, heavier and/or odd-shaped medical items 180. Typically, the adhesiveness of the polymer component 170 of this disclosure (and thus of the adhesive medical tray member 150 herein) will desirably range from about 25 $g_f/cm^2$ to about 150 $g_f/cm^2$ as measured by the Adhesiveness & Cohesiveness Test, such as about 40 $g_f/cm^2$ to about 100 $g_f/cm^2$ to provide improved benefits.

Another unique advantage of the adhesive medical tray member 150 herein resides in the manner in which the polymer component 170 will adhesively interact with medical items 180 which are adhesively attached thereto. The polymer component's 170 adhesive interaction with medical items 180, when such items 180 are placed thereupon, typically exhibits a slight initial increase in adhesiveness within about 5 to about 10 seconds after the initial adhesive attachment of a medical item 180 to the polymer component 170, which is then followed by a stabilization to about 90% of its maximum or ultimate adhesive attraction within about 60 seconds after the initial adhesive attachment of the item 180 to the polymer component 170. This slight change in adhesiveness may be indicative of an intermolecular realignment, coordinate covalent bonding, polarization of the plasticizing components, or some other molecular interaction therein. This subsequent adhesive increase may also be due to the viscoelastomeric properties of the polymer component 170 which, due to adhesive cradling of an adhered medical item 180, will provide added interfacing surface contacting area with the adhered item 180, resulting in an increase and subsequent stabilization of the adhesive attraction therebetween.

Another unique advantage of the adhesive medical tray member 150 herein resides in the retention of at least its adhesiveness and cohesiveness properties. Surprisingly, the polymer component 170 of the adhesive medical tray member 150 as provided by this invention retains a substantially unchanged degree of adhesiveness and cohesiveness with respect to adhered medical items 180 over prolonged periods of time (e.g., at least six (6) weeks or more), such as measured by the Adhesiveness & Cohesiveness Test. This provides another significant advantage over conventional adhesive products (wherein the adhesiveness and/or cohesiveness tends to degrade over time).

In addition, the polymer component 170 of the adhesive medical tray member 150 herein also exhibits advantageously unique cohesiveness properties. For example, upon exposure to a counteracting force sufficient to overcome the adhesive attraction between a medical item 180 and the adhesive medical tray member 150 herein (e.g., pulling an adhesively engaged item 180 away from the adhesive medical tray member 150 to disengage the item 180), the compositional cohesiveness of the polymer component 170 will tenaciously retain its viscoelastomeric structural integrity by cohesively releasing substantially cleanly (i.e., without leaving substantially any polymeric residue) from the item 180 and then returning to its original innate form as prior to engagement of the item 180. This provides a significant advantage with respect to reusability and effectiveness of the adhesive medical tray member 150, as compared to conventional adhesive products (which typically do not return to their same innate form and/or leave visible residue upon a detached item and/or are not reusable (i.e., without experiencing a reduction in effectiveness)).

In addition, the polymer component 170 of the adhesive medical tray member 150 herein also exhibits advantageously unique releasability properties. More particularly, the polymer component 170 possesses a tenacious internal compositional cohesiveness which provides an ability to release substantially cleanly away from a medical item 180 upon which it comes into contact, substantially without leaving any residue of the polymer component 170 remaining on the surface of the item 180. (As used herein, the term "substantially" means that on a microscopic level, a nominal amount of polymeric residue may potentially be detectable.) Indeed, upon exposure to a suitable adhesive separating release force (e.g., pulling an adhesively engaged medical item 180 away from the adhesive medical tray member 150), the compositional cohesiveness of the polymer component 170 will tenaciously retain its viscoelastic structural integrity by separating substantially cleanly from the surface of a medical item 180 upon which it has come into contact (i.e., without leaving more than a trace of polymeric residue upon the surface, and more typically no trace of polymeric residue). Accordingly, upon adhesive separation from such surface of a medical item 180, the polymer component 170 will return to its substantially intact and innate form as prior to adherence of the item 180, while leaving no more than a minuscule amount of polymeric residue adhering upon the item 180. More typically, upon separation from the surface of a medical item 180, there will exist no polymeric residue remaining upon the item 180 whatsoever. This provides yet another significant advantage over conventional adhesive products (which typically leave a visually detectable amount of residue upon the surface of an item upon which it comes into contact).

During the removal of a medical item 180 from the adhesive medical tray member 150 of the inventive articulating medical stand 100 of the present disclosure, it has been observed herein that the polymer 170 tends to pull away from the surface of the item 180 until the polymer 170 completely separates (i.e., breaks cleanly away) from the surface, and then the polymer component 170 forthrightly cohesively returns to its original or innate form as prior to the item's 180 adherence thereto. The extent of temporary distortion exhibited by the polymer component 170 upon exposure to separation forces from the surface of a medical item 180 will depend largely upon the adhesiveness, cohesiveness and viscoelastic properties of the polymer component 170. It has been further observed herein that, upon coming into contact with a surface of a medical item 180, a polymer component 170 herein having relatively higher adhesiveness values will physically tend to tenaciously string-out (similar to the pulling of heated candy taffy) until a clean adhesive, but cohesive, separation ultimately occurs from the surface of the item 180, whereupon the polymer component 170 then returns to its original innate form, preferably leaving no polymeric residue upon the item 180.

In addition, the polymer component 170 of the adhesive medical tray member 150 herein also exhibits antimicrobial properties which may be critical for its intended use in the medical field. For example, the polymer 170 can neutralize microbial pathogens (e.g., viruses, bacteria, germs, etc.) which may be present upon the engaged surfaces of a medical item 180 or a user's hand (despite the presence of gloves). This provides still another significant advantage over conventional adhesive products (which typically do not exhibit such antimicrobial properties).

In addition, the polymer component 170 of the adhesive medical tray member 150 herein also exhibits unique cleansability properties, thus allowing a soiled or contaminated adhesive medical tray member 150 to be quickly cleaned and re-sterilized. For example, due to its adhesive nature, the polymer component 170 can have a tendency to adhesively attract contaminants, such as airborne contaminants (e.g., dust, lint, debris, etc.) and/or patient derived contaminants (e.g., blood, saliva, hair, keratinocytes, etc.), which can potentially diminish adhesiveness (and potentially antimicrobial effectiveness) over time. However, the original adhesiveness and antimicrobial properties of the polymer component 170 can be easily restored via conventional washing and/or other suitable contaminant removal techniques and sterilization techniques. For example, unlike conventional adhesive products which must be discarded upon contamination (often after merely a single use), the adhesive medical tray member 150 comprising the polymer component 170 can be removed from the inventive articulating medical stand 100 and then can be cleansed from contaminants and restored to its substantially original adhesive, cohesive and antimicrobial efficacy. Surprisingly, conventional washing with water or with a solution of water and common soap (e.g., rinsing, hand-washing, scrubbing, washing machines, dishwashers, etc.), as well as autoclaving (i.e., applying high pressure steam), can be effectively utilized to eradicate and remove contaminants therefrom and thereby permit fully functional continued use or re-use of the cleansed adhesive medical tray member 150. This provides yet another significant advantage over conventional adhesive products (which typically do not exhibit such cleansability and reusability capabilities). Accordingly, the present invention can be considered environmentally friendly, and may also be considered as "green" technology.

In some embodiments, the releasably adhesive and cohesive viscoelastomeric thermoset polymer component 170 can be prefabricated into a desired form (e.g., desired shape profile, dimensions, etc.) using various techniques as known to persons having ordinary skill in the art. Such prefabrication techniques can include, but are not limited to, casting, molding, pouring, injecting, film forming, brushing, spraying, and the like. Prefabrication of the polymer component 170 typically comprises first preparing the thermosetting reaction media, then utilizing a desirable prefabrication process while the reaction media is in a liquid or semi-liquid (i.e., partially cured) form, and subsequently allowing the reaction media to fully cure in a freestanding polymer component 170. This can be accomplished, inter alia, by disposing liquid reaction media (i.e., uncured or partially cured) into a suitable mold and then curing the reaction media to form the polymer component 170, or by pouring the reaction media onto a suitable surface (e.g., a flat surface) as a layer of the reaction media, allowing it to fully cure, and then cutting the polymer into components therefrom. Other methods for forming the polymer component 170 which will be apparent to persons having ordinary skill in the art are also suitable, without departing from the scope of the invention. Such a prefabricated form of the polymer component 170 can have any shape profile and dimensions as may be desired without departing from the scope of the invention, including those known to persons having ordinary skill in the art, such as a pad, a substrate, a strip, a sheet, a film, an overlay, a mat, a random shape, and the like. Such a prefabricated polymer component 170 can then be applied to the tray component 154 of the adhesive medical tray member 150 (and subsequently removed, then subsequently re-applied, etc.).

It has been discovered herein that certain materials, such as silicone-coated materials or halogenated polymers (e.g., polyvinylchloride (PVC)) (except for special formulations) are generally less adhesively compatible (as compared to most other materials) with the adhesiveness properties of the releasably adhesive and cohesive viscoelastomeric thermoset polymer component 170 herein (i.e., the polymer component 170 does not adhere as well to such materials). As a result, such less adhesively compatible materials can provide excellent release properties from the polymer component 170, which renders such materials particularly effective for use as a mold material (which can be utilized to cure the reaction media and thus prefabricate the polymer component 170), as well as for removable protective coverings for the prefabricated polymer component 170. However, it should be understood that if such less adhesively compatible materials have a porous, fabric or patterned structure, such structures can provide anchoring or penetration sites for the polymer component 170 (e.g., due to the polymer's 170 viscoelastic nature), thus increasing the adhesion between the polymer 170 and such materials, rendering such materials to be unsuitable for use as a mold material or removable protective covering.

In other embodiments, the releasably adhesive and cohesive viscoelastomeric thermoset polymer component 170 can be formed by applying liquid reaction media directly upon the tray component 154 and allowing it to fully cure in situ to form the adhesive medical tray member 150 (as opposed to prefabricating the polymer component 170 and then subsequently applying it to the tray component 154). In comparison to the embodiment described above, the adhesive medical tray member 150 can be presented in a "pre-made" form, rather than requiring a user or manufacturer to apply a prefabricated polymer component 170 onto a tray component 154 to form the adhesive medical tray member 150.

In preferred aspects of this embodiment, the releasably adhesive and cohesive viscoelastomeric thermoset polymer component 170 is essentially equivalent to the polymer as described above for the prefabricated embodiment. However, rather than prefabricating the polymer component 170, the polymer component 170 can be formed upon the tray component 154. This can be accomplished by first disposing a quantity of uncured or partially cured reaction media (i.e., while the reaction media is still in liquid form) directly onto a surface of tray component 154, and then allowing the reaction media to fully cure in-situ to form the polymer component 170, and thus the adhesive medical tray member 150. It has been discovered herein that in such "in situ" embodiments, the polymer component 170 tends to form a stronger bond with tray component 154 upon which it is applied, as compared to merely adhesively bonding a prefabricated polymer component 170 to the tray component 154. It is believed that in such in situ embodiments, attachment of the polymer component 170 to the tray component 154 includes additional bonding (e.g., chemical bonding), in addition to the adhesive bonding common to both the in situ embodiments and the prefabricated embodiments of the polymer component 170. Accordingly, in this in situ embodiment, the polymer component 170 can be difficult to remove from the tray component 154.

The reaction media of this in situ embodiment can be applied to the tray component 154 using techniques as would be known to persons having ordinary skill in the art, including pouring, printing, calendaring, casting, brushing, spraying, dipping, and the like. The polymer component 170 of this in situ embodiment can comprise any functional shape profile or form, such as a coating, a strip, a pattern, a shape, a film, and the like, without departing from the scope of the invention.

Essentially all of the properties and advantages of the prefabricated polymer component 170 embodiment described above apply equally to the in situ formed polymer component 170 of this embodiment, including the viscoelasticity, adhesiveness, releasability, cohesiveness, stability, cleansability and antimicrobial properties. However, while reusability is an option for this embodiment, it is less likely to be utilized as compared to the prefabricated embodiment. Also, similar to the prefabricated embodiment, the adhesiveness of the polymer component 170 of this in situ embodiment can likewise be formulated to be about 25 $g/cm^2$ to about 150 $g/cm^2$, as measured by the Adhesiveness & Cohesiveness Test, such as about 40 $g/cm^2$ to about 100 $g/cm^2$ to provide improved benefits.

In some aspects, due to at least the inherently adhesive nature of the, as well as its intended use in hygienic or sterilized environment, it may be desirable to dispose an optional removable protective covering member (not shown) upon the prefabricated polymer component 170, or upon the top side 152 of the adhesive medical tray member 150 when the polymer component 170 has already been applied or has been formed in situ. For example, such protective covering member can allow for effective shipment of the prefabricated polymer component 170 or the adhesive medical tray member 150, ease of handling the prefabricated polymer component 170 or the adhesive medical tray member 150 (e.g., preventing adhesion to a user's hands), and can prevent undesired contamination of the prefabricated polymer component 170 or the adhesive medical tray member 150 by contaminants prior to its intended use. In some aspects, a protective covering member can also be useful as packaging materials for the invention. Such protective covering member can comprise any suitable material which can be completely (and preferably relatively easily) removed from the prefabricated polymer component 170 or the adhesive medical tray member 150 without leaving any covering materials during removal. For example, materials which have a relatively low or incompatible adhesive affinity to the polymer component 170 can be used with the invention to provide a suitable protective covering member. Examples of a suitable protective covering member can include, but is not limited to, silicone-coated substrates, polyvinyl chloride (PVC) films, paraffin-coated substrates, TEFLON-coated substrates, and the like, which tend to be less adhesively compatible with the polymer component 170 than most other materials.

Returning now to FIG. 1, and with additional reference to FIGS. 7A-7E, the adhesive medical tray member 150 is intended to be attached to the tray receiving element 148 of the tray mounting member 140. Any suitable removable attachment means known to persons having ordinary skill in the art can be utilized without departing from the scope of the invention, including but not limited to tension, friction, screws, bolts, clips, springs, snaps, magnets, hook-and-loop, releasable adhesives, and the like, and combinations thereof. In the case of releasable adhesives, it may be desirable to utilize an additional amount of the releasably adhesive and cohesive viscoelastomeric thermoset polymer component 170 to accomplish such attachment. For example, in some aspects, the additional polymer component 170 can be disposed upon at least a portion of the bottom side 151 of the adhesive medical tray member 150 (see e.g., FIG. 7C). In other aspects, the additional polymer component 170 can be disposed upon optional side elements 155 and/or lip elements 156 (if present) of the adhesive medical tray member 150 (see e.g., FIG. 7D). In still other aspects, the additional polymer component 170 can be placed any exposed surface of the adhesive medical tray member 150 which is not intended for use with medical items 180 (see e.g., FIG. 7E).

As referenced above, conventional (i.e., existing) medical stands (e.g., Mayo stands) typically provide either no means for dimensional adjustment at all, or are limited to providing height adjustment at most. Thus, the multidirectional adjustment capabilities (including the capability of adjustment in all dimensional axes (i.e., x-axis, y-axis and z-axis)), as well as the releasable adhesiveness and antimicrobial attributes, of the inventive articulating medical stand 100 of the present disclosure provide for unheralded advantages over conventional medical stands. Indeed, the effectiveness and efficiencies gained by use of the present invention 100 may change the way medical procedures are practiced. Such advantages include, but are not limited to, cost savings, time savings, decreased contamination of dropped medical items 180, improved ergonomics for the user, increased control of a medical procedure by a user, closer proximity of medical items 180 to the location of use, reduced personnel requirements, green technology, and the like.

The invention also includes a method for making an inventive articulating medical stand 100. The method comprises:
A. providing a lower horizontal support member 120 comprising a top side 124 and a bottom side 122;
B. providing vertical support member 110 comprising a lower end 112, an upper end 114, and a longitudinal axis 110L, wherein the vertical support member 110 is capable of vertical adjustment along the longitudinal axis 110L;
C. providing an upper horizontal support member 130 comprising a first end 132, a second end 134, a longitudinal axis 130, and a longitudinal length $130_X$, wherein the horizontal support member 130 is capable of axial rotational adjustment about the longitudinal axis 130L;
D. providing a tray mounting member 140 comprising a housing support element 144, an adjustable connector element 146, and a tray receiving element 148;
E. providing an adhesive medical tray 150 comprising a top side 152 and a bottom side 151, wherein the top side 152 of the adhesive medical tray 150 comprises an adhesive component 160 capable of releasably attaching medical items 180;
F. attaching the lower end 112 of the vertical support member 110 to the top side 124 of the lower horizontal support member 120;
G. attaching the first end 132 of the upper horizontal support member 130 proximate to the upper end 114 of the vertical support member 110;
H. slideably attaching the housing support element 144 of the tray mounting member 140 to the upper horizontal support member 130; and
I. removably attaching the adhesive medical tray 150 to the tray receiving element 148 of the tray mounting member 140;
wherein the tray mounting member 140 is capable of longitudinal adjustment along the longitudinal length $130_X$ of the upper horizontal support member 130;
wherein the tray mounting member 140 can rotate with the upper horizontal support member 130; and
wherein the tray mounting member 140 is capable of angular adjustment with respect to the upper horizontal support member 130.

In some aspects of this embodiment, the adhesive component 160 comprises a releasably adhesive and cohesive viscoelastomeric thermoset polymer component 170. In further aspects of this embodiment, the releasably adhesive and cohesive viscoelastomeric thermoset polymer component 170 is formed from a thermosetting reaction media comprising:
A. about 2 wt % to about 10 wt % isocyanate prepolymer;
B. about 35 wt % to about 75 wt % polyols; and
C. about 10 wt % to about 60 wt % plasticizer;
wherein the polyols comprise about 1 wt % to about 65 wt % straight chain polyols based on the total reaction media weight and about 3 wt % to about 50 wt % crosslinking polyols based on the total reaction media weight, and wherein the plasticizer comprises about 10 wt % to less than about 45 wt % epoxidized triglyceride plasticizer based on the total reaction media weight and 0 wt % to about 40 wt % viscosity-reducing plasticizer based on the total reaction media weight. In other aspects of this embodiment, the adhesive medical tray 150 comprises an adhesiveness of about 25 g/cm² to about 150 g/cm² as measured by the Adhesiveness & Cohesiveness Test.

The invention also includes a method for using an inventive articulating medical stand 100. The method comprises:

A. providing an articulating medical stand 100 comprising a lower horizontal support member 120 having a top side 124 and a bottom side 122, a vertical support member 110 comprising a lower end 112, an upper end 114 and a longitudinal axis 110, wherein the lower end is attached to the top side 124 of the lower horizontal support member 120, an upper horizontal support member 130 comprising a first end 132, a second end 134, a longitudinal axis 130, and a longitudinal length 130$_X$ wherein the first end 132 is attached proximate to the upper end 114 of the vertical support member 110, and a tray mounting member 140 comprising a housing support element 144, an adjustable connector element 146, and a tray receiving element 148 wherein the housing support element 144 is slideably connected to the upper horizontal support member 130;

B. providing an adhesive medical tray member 150 comprising a tray component 154 having a top side 158 and a bottom side 157, and further comprising an adhesive component 160 disposed upon the top side 158 thereof;

C. attaching the adhesive medical tray member 150 to the tray receiving element 148 of the tray mounting member 140 to form the inventive articulating medical stand 100;

D. disposing medical items 180 upon the top side 152 of the adhesive medical tray member 150 to form releasably attached medical items;

E. multi-directionally adjusting the inventive articulating medical stand 100 such that the attached medical items 180 are located at a desired location with respect to the user;

F. detaching a medical item 180 from the adhesive medical tray member 150 of the articulating medical stand 100 for use; and G. re-attaching the medical item 180 to the adhesive medical tray member 150 of the articulating medical stand 100 after use.

wherein the vertical support member 110 is capable of vertical adjustment along its longitudinal axis 110L, wherein the upper horizontal support member 130 is capable of axial rotational adjustment about its longitudinal axis 130L, wherein the tray mounting member 140 is capable of linear adjustment along the longitudinal length 130$_X$ of the upper horizontal support member 130, wherein the tray mounting member 140 is capable of rotational adjustment with the upper horizontal support member 130, and wherein the tray mounting member 140 is capable of angular adjustment with respect to the upper horizontal support member 130.

In some aspects of this embodiment, the vertical support member 110 is further capable of axial rotational adjustment about its longitudinal axis 110L. In other aspects of this embodiment, the adhesive component 160 comprises a releasably adhesive and cohesive viscoelastomeric thermoset polymer component 170. In further aspects, the releasably adhesive and cohesive viscoelastomeric thermoset polymer component is formed from a thermosetting reaction media comprising:

A. about 2 wt % to about 10 wt % isocyanate prepolymer;
B. about 35 wt % to about 75 wt % polyols; and
C. about 10 wt % to about 60 wt % plasticizer;

wherein the polyols comprise about 1 wt % to about 65 wt % straight chain polyols based on the total reaction media weight and about 3 wt % to about 50 wt % crosslinking polyols based on the total reaction media weight, and wherein the plasticizer comprises about 10 wt % to less than about 45 wt % epoxidized triglyceride plasticizer based on the total reaction media weight and 0 wt % to about 40 wt % viscosity-reducing plasticizer based on the total reaction media weight. In other aspects of this embodiment, the adhesive medical tray of the articulating medical stand comprises an adhesiveness of about 25 g/cm$^2$ to about 150 g/cm$^2$ as measured by the Adhesiveness & Cohesiveness Test.

The present invention may be better understood with reference to the following example.

EXAMPLES

Example 1

A stainless steel lower horizontal support member 120 was provided. The lower horizontal support member 120 was rectangular in shape (similar to the shape of a wooden 2×4). The lower horizontal support member 120 comprised two (2) casters 126 disposed upon the bottom side 122, proximate to the distal ends thereof, which are primarily utilized when moving the articulating medical stand 100 from one geographical location to another. In addition, disposed upon one longitudinal side of the lower horizontal support member 120 were two (2) horizontal protruding members 128 configured in a general "V" shape which served as legs, which are primarily utilized when the articulating medical stand is at rest. The lower horizontal support member 120 of this Example 1 generally resembled that shown in FIGS. 1 and 3.

A stainless steel vertical support member 110 was provided. The lower end 112 of the vertical support member 110 was then attached (via spot welding) to a central portion of the top side 124 of the lower horizontal support member 120. The vertical support member 110 comprised a core-and-sheath configuration. While the overall vertical support member 110 had a generally cylindrical shape profile, the core portion comprised a plurality of longitudinal planar (i.e., flat) surfaces, such that a cross-section resembled a decagon. Accordingly, the vertical support member 110 could be telescopically extended or retracted vertically, and the core portion could be rotated within the sheath portion. A set screw (i.e., a threaded rod with a knob) was utilized to the maintain an adjusted position of the core portion of the vertical support member 110 with respect to the sheath portion. The vertical support member 110 of this Example 1 generally resembled that shown in FIGS. 1 and 2.

A stainless steel upper horizontal support member 130 was provided. While the overall upper horizontal support member 130 had a generally cylindrical shape profile, the core portion comprised a plurality of longitudinal planar (i.e., flat) surfaces, such that a cross-section resembled a decagon. A first end 132 of the upper horizontal support member 130 was attached to the upper end 114 of the vertical support member 110 via a coupling that allowed the upper horizontal support member 130 to rotate therein. In this Example 1, a set screw (i.e., a threaded rod with a knob) was utilized to the maintain a rotated position of the upper horizontal support member 130. The upper horizontal support member 130 of this Example 1 generally resembled that shown in FIGS. 1, 4 and 5.

A stainless steel coupling in the form of a housing component 144A including a nylon insert and having a support base component 144B integrated upon its top side was mated onto the second end 134 of the upper horizontal support member 130. The housing component 144A was configured such that it could slide (with some resistance via the nylon insert) along the length $130_X$ of the upper horizontal support member 130. A stainless steel rotationally adjustable connector element 146 comprising an adjustment component 146A, a set component 146B and a support component 146C disposed upon its top side was then mounted and fastened to the support base component 144B. A stainless steel tray receiving element 148 comprising a frame component 148A and a crossbeam support component 148B was then fastened to the support base component 144B located on the top side of the adjustable connector element 146 via the crossbeam support component 148B, thus forming a tray mounting member 140. The frame component 148A comprised tubular stainless steel and had a rectangular frame-like configuration. The crossbeam support component 148B was a generally flat strip of stainless steel wherein the end portions curved upward, and the ends of the crossbeam support component 148B were welded to the bottom side of the frame component 148A, such that the tray receiving element 148 comprised a depth. Upon attachment to the adjustable connector element 146, the tray receiving element 148 of the tray mounting member 140 could be angularly adjusted with respect to the longitudinal axis 130L of the upper horizontal support member 130. The tray mounting member 140 of this Example 1 generally resembled that shown in FIGS. 1 and 5.

An adhesive medical tray member 150 comprising a tray component 154 and an adhesive component 160 was then provided. The tray component 154 was a conventional stainless steel Mayo tray. However, liquid thermosetting reaction media was disposed into the top side 152 of the tray component 154 and then cured to form a polymeric adhesive component 160. The adhesive medical tray member 150 was then placed into the tray receiving element 148 of the tray mounting member 140 (which had similar dimensions to the adhesive medical tray member 150) using slight pressure, such that tension and friction removably secured the adhesive medical tray member 150, thus forming the inventive articulating medical stand 100 of the present disclosure. Accordingly, the adhesive medical tray member 150 (by virtue of the inventive articulating medical stand 100) could be adjusted through all axes (i.e., x-axis, y-axis and z-axis).

As referenced above, the adhesive component 160 was formed from a thermosetting reaction media. The thermosetting reaction media was formulated to form a releasably adhesive and cohesive viscoelastomeric thermoset polymer component 170, which was prepared as follows in Table 1 by uniformly admixing together a two-part solution component mix (Part A Solution and Part B Solution) comprising:

TABLE 1

| Thermosetting Reaction Media | |
|---|---|
| Part A Solution-Ingredients: | Percent by Weight: |
| Methylene diphenyl diisocyanate-based glycol prepolymer (ElastoCAST TQZP23 available from BASF Corporation) | 6.04 wt % |
| Epoxidized triglyceride plasticizer (epoxidized soybean oil) | 42.62 wt % |
| Part B Solution-Ingredients: | Percent by Weight: |
| Polyether diol (ElastoCAST C-4057 available from BASF Corporation) | 16.14 wt % |
| Polyether triol (ElastoCAST C-4018 available from BASF Corporation) | 33.82 wt % |

TABLE 1-continued

| Thermosetting Reaction Media | |
|---|---|
| Colorant blend (1 part STAN-TONE 42ET02 Blue (available from Avient Corporation, having a place of business located in Avon Lake, Ohio, USA) and 5 parts epoxidized soybean oil) | 0.04 wt % |
| UV Inhibitor (Tinuvin B 75 available from BASF Corporation) | 1.23 wt % |
| Slow-acting Catalyst (COSCAT 83 available from Vertellus Holdings LLC) | 0.11 wt % |
| Total | 100% |

The Part A ingredients were mixed to form the Part A Solution. Separately, the Part B ingredients were mixed to form the Part B Solution. Equal parts (i.e., a 1:1 ratio) of the Part A Solution and the Part B Solution were then combined and blended through a static mixer using metering pumps to form a thermosetting reaction media. While still in liquid form, a quantity of the resulting reaction media of this Example 1 was disposed into the top side 152 of the tray member 150 until a thickness of about 2 mm was obtained. The reaction media was then allowed to fully cure in situ to form the releasably adhesive and cohesive viscoelastomeric thermoset polymer component 170.

The adhesiveness and cohesiveness of the adhesive component 160 of this Example 1 was tested in accordance with the Adhesiveness & Cohesiveness Test set forth herein using a test sample 330 of the adhesive component 160. The average adhesiveness was measured to be about 75 $g_f/cm^2$. It was also noted that no observable polymeric residue remained upon the surface 345 of the cylinder 340 component of the testing apparatus 300 during each test iteration.

Lastly, several medical items 180 in the form of a metallic forceps, a metallic tweezers and a plastic syringe holder were then placed on the top side 152 of the tray member 150. Each medical item 180 was then subsequently removed and reattached several times. It was observed that the medical items 180 each detached relatively easily when a sufficient counteracting force was applied, and that the adhesive component 160 returned to its original innate state after each medical item 180 was detached. It was also observed that subsequent reattachments of the medical items 180 after repeated removals did not exhibited any diminishing adhesion force (i.e., adhesiveness) of the medical items 180. Upon visual inspection of each medical item 180, it was further observed that no polymeric residue was visually detectable upon any of the items 180.

It will be appreciated that details of the foregoing examples, given for purposes of illustration, are not to be construed as limiting the scope of the present invention. Although only a few exemplary embodiments of the present invention have been described in detail above, persons having skill in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of the present invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An articulating medical stand comprising a lower horizontal support member, a vertical support member and an upper horizontal support member;
   wherein the lower horizontal support member comprises a top side and an opposing bottom side distal to the top side;
   wherein the vertical support member comprises an upper end, an opposing lower end distal to the upper end, a longitudinal length and a longitudinal axis;
   wherein the upper horizontal support member comprises a first end, an opposing second end distal to the first end, a longitudinal length and a longitudinal axis;
   wherein the lower end of the vertical support member is attached to the top side of the lower horizontal support member;
   wherein the first end of the upper horizontal support member is rotatably disposed through a housing member which is attached to the upper end of the vertical support member;
   wherein the vertical support member is vertically adjustable along its longitudinal length;
   wherein the upper horizontal support member is axially rotatable about its longitudinal axis; and
   wherein the articulating medical stand can be utilized while disposed upon a floor.

2. The articulating medical stand of claim 1, wherein the vertical support member is axially rotatable about its longitudinal axis.

3. The articulating medical stand of claim 2 further comprising a tray mounting member.

4. The articulating medical stand of claim 3, wherein the tray mounting member comprises a housing support element, an adjustable connector element, and a tray receiving element;
   wherein the housing support element is slideably connected to the upper horizontal support member such that the tray mounting member can be repositioned along the longitudinal length of the upper horizontal support member and the tray mounting member can further rotate with the upper horizontal support member;
   wherein the adjustable connector element is attached to the housing support element;
   wherein the tray receiving element is attached to the adjustable connector element;
   wherein the adjustable connector element is capable of providing angular adjustment of the tray receiving element; and
   wherein the tray receiving element is adapted to receive a medical tray member.

5. The articulating medical stand of claim 4, wherein the tray receiving element further comprises a crossbeam support component, and wherein the tray receiving element is attached to the adjustable connector element via the crossbeam support component.

6. The articulating medical stand of claim 4, wherein the articulating medical stand is in the form of an articulating Mayo stand.

7. The articulating medical stand of claim 4 further comprising a medical tray member, wherein the medical tray member is removably attached to the tray mounting member.

8. The articulating medical stand of claim 7, wherein the medical tray member is in the form of an adhesive medical tray member.

9. The articulating medical stand of claim 8, wherein the adhesive medical tray member comprises a top side and a bottom side, and wherein an adhesive component is disposed upon at least a portion of the top side of the adhesive medical tray member.

10. The articulating medical stand of claim 9, wherein the adhesive medical tray member further comprises a side element disposed upon at least a portion of a perimeter of the top side of the adhesive medical tray member.

11. The articulating medical stand of claim 10, wherein the adhesive medical tray member further comprises a lip element disposed upon an upper edge portion of the side element.

12. The articulating medical stand of claim 9, wherein the adhesive medical tray comprises an adhesiveness of about 25 $g/cm^2$ to about 150 $g/cm^2$.

13. The articulating medical stand of claim 1, wherein the adhesive medical tray member comprises an adhesive component thickness of about 0.5 mm to about 13 mm.

14. The articulating medical stand of claim 9, wherein the adhesive component comprises a releasably adhesive and cohesive viscoelastomeric thermoset polymer component.

15. The articulating medical stand of claim 12, wherein the releasably adhesive and cohesive viscoelastomeric thermoset polymer component is formed from a thermosetting reaction media comprising:
   A. about 2 wt % to about 10 wt % isocyanate prepolymer;
   B. about 35 wt % to about 75 wt % polyols; and
   C. about 10 wt % to about 60 wt % plasticizer;
   wherein the polyols comprise about 1 wt % to about 65 wt % straight chain polyols based on the total reaction media weight and about 3 wt % to about 50 wt % crosslinking polyols based on the total reaction media weight; and
   wherein the plasticizer comprises about 10 wt % to less than about 45 wt % epoxidized triglyceride plasticizer based on the total reaction media weight and 0 wt % to about 40 wt % viscosity-reducing plasticizer based on the total reaction media weight.

16. The articulating medical stand of claim 15, wherein the isocyanate prepolymer comprises diisocyanate.

17. The articulating medical stand of claim 15, wherein the thermosetting reaction media further comprises a straight chain polyol to crosslinking polyol weight ratio of about 3:1 to about 1:3.

18. The articulating medical stand of claim 15, wherein the straight chain polyols comprise polyether diol and the crosslinking polyols comprise polyether triol.

19. The articulating medical stand of claim 15, wherein the epoxidized triglyceride plasticizer comprises epoxidized vegetable oil plasticizer.

20. The articulating medical stand of claim 15, wherein the viscosity-reducing plasticizer comprises an ester plasticizer.

21. The articulating medical stand of claim 15, wherein the releasably adhesive and cohesive viscoelastomeric thermoset polymer component is applied to the adhesive medical tray member in a prefabricated form.

22. The articulating medical stand of claim 15, wherein the thermosetting reaction media has been disposed upon the top side of the adhesive medical tray member while in liquid form, and then allowed to fully cure in-situ to form the releasably adhesive and cohesive viscoelastomeric thermoset polymer component.

23. The articulating medical stand of claim 14, wherein the adhesive medical tray member further comprises releasably adhesive and cohesive viscoelastomeric thermoset polymer component disposed upon the bottom side.

24. A method of making an articulated medical stand, comprising:
   A. providing a lower horizontal support member comprising a top side and a bottom side;
   B. providing a vertical support member comprising a lower end, an upper end, and a longitudinal axis, wherein the vertical support member is capable of vertical length adjustment along the longitudinal axis, and wherein the vertical support member further comprises a housing member disposed at the upper end;
   C. providing an upper horizontal support member comprising a first end, a second end, a longitudinal axis and a longitudinal length, wherein the horizontal support member is capable of axial rotational adjustment about the longitudinal axis;
   D. providing a tray mounting member comprising a housing support element, an adjustable connector element, and a tray receiving element;
   E. providing an adhesive medical tray member comprising a top side and a bottom side, wherein the top side of the adhesive medical tray member comprises an adhesive component capable of releasably attaching medical items;
   F. attaching the lower end of the vertical support member to the top side of the lower horizontal support member;
   G. disposing the first end of the upper horizontal support member through the housing member at the upper end of the vertical support member such that the upper horizontal support member is axially rotatable therein;
   H. slideably attaching the housing support element of the tray mounting member to the upper horizontal support member; and
   I. removably attaching the adhesive medical tray member to the tray receiving element of the tray mounting member;
   wherein the tray mounting member is capable of longitudinal adjustment along the longitudinal length of the upper horizontal support member;
   wherein the tray mounting member can rotate with the upper horizontal support member; and
   wherein the tray mounting member is capable of angular adjustment with respect to the upper horizontal support member.

25. The method of claim 24, wherein the adhesive component comprises a releasably adhesive and cohesive viscoelastomeric thermoset polymer component.

26. The method of claim 25, wherein the releasably adhesive and cohesive viscoelastomeric thermoset polymer component is formed from a thermosetting reaction media comprising:
   A. about 2 wt % to about 10 wt % isocyanate prepolymer;
   B. about 35 wt % to about 75 wt % polyols; and
   C. about 10 wt % to about 60 wt % plasticizer;
   wherein the polyols comprise about 1 wt % to about 65 wt % straight chain polyols based on the total reaction media weight and about 3 wt % to about 50 wt % crosslinking polyols based on the total reaction media weight; and
   wherein the plasticizer comprises about 10 wt % to less than about 45 wt % epoxidized triglyceride plasticizer based on the total reaction media weight and 0 wt % to about 40 wt % viscosity-reducing plasticizer based on the total reaction media weight.

27. The method of claim 24, wherein the adhesive medical tray comprises an adhesiveness of about 25 $g/cm^2$ to about 150 $g/cm^2$.

28. A method for using an articulating medical stand comprising:
   A. Providing an articulating medical stand comprising a lower horizontal support member having a top side and a bottom side, a vertical support comprising a lower end, an upper end and a longitudinal axis wherein the lower end is attached to the top side of the lower horizontal support member and further comprising a housing member disposed at the upper end thereof, an upper horizontal support member comprising a first end, a second end, a longitudinal axis and a longitudinal length wherein the first end is rotatably disposed through the housing member at the upper end of the vertical support member, and a tray mounting member comprising a housing support element, an adjustable connector element, and a tray receiving element wherein the housing support element is slideably connected to the upper horizontal support member;
   B. providing an adhesive medical tray member comprising a tray component having a top side and a bottom side, and further comprising an adhesive component disposed upon the top side thereof;
   C. attaching the adhesive medical tray member to the tray receiving element of the tray mounting member to form the articulating medical stand;
   D. disposing medical items upon the top side of the adhesive medical tray member to form releasably attached medical items;
   E. multi-directionally adjusting the articulating medical stand such that the attached medical items are located at a desired location with respect to the user; and
   F. detaching a medical item from the adhesive medical tray member of the articulating medical stand for use;
   wherein the vertical support member is capable of vertical adjustment along its longitudinal axis;
   wherein the upper horizontal support member is capable of axial rotational adjustment about its longitudinal axis;
   wherein the tray mounting member is capable of linear adjustment along the longitudinal length of the upper horizontal support member;
   wherein the tray mounting member is capable of rotational adjustment via the upper horizontal support member, and
   wherein the tray mounting member is capable of angular adjustment with respect to the upper horizontal support member.

29. The method of claim 28, further comprising re-attaching the medical item to the adhesive medical tray member of the articulating medical stand after use.

30. The method of claim 28, wherein the vertical support member is further capable of axial rotational adjustment about its longitudinal axis.

31. The method of claim 28, wherein the adhesive component comprises a releasably adhesive and cohesive viscoelastomeric thermoset polymer component.

32. The method of claim 30, wherein the releasably adhesive and cohesive viscoelastomeric thermoset polymer component is formed from a thermosetting reaction media comprising:
- A. about 2 wt % to about 10 wt % isocyanate prepolymer;
- B. about 35 wt % to about 75 wt % polyols; and
- C. about 10 wt % to about 60 wt % plasticizer;
- wherein the polyols comprise about 1 wt % to about 65 wt % straight chain polyols based on the total reaction media weight and about 3 wt % to about 50 wt % crosslinking polyols based on the total reaction media weight; and
- wherein the plasticizer comprises about 10 wt % to less than about 45 wt % epoxidized triglyceride plasticizer based on the total reaction media weight and 0 wt % to about 40 wt % viscosity-reducing plasticizer based on the total reaction media weight.

33. The method of claim 28, wherein the adhesive medical tray of the articulating medical stand comprises an adhesiveness of about 25 $g_f/cm^2$ to about 150 $g_f/cm^2$.

* * * * *